(12) United States Patent
Dalton et al.

(10) Patent No.: US 12,098,172 B2
(45) Date of Patent: Sep. 24, 2024

(54) COMPOSITIONS AND METHODS FOR TARGETING MASAs TO TREAT CANCERS WITH SPLICEOSOME MUTATIONS

(71) Applicant: The Johns Hopkins University, Baltimore, MD (US)

(72) Inventors: William Brian Dalton, Baltimore, MD (US); Ben Ho Park, Perry Hall, MD (US); Eric Christenson, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 820 days.

(21) Appl. No.: 16/635,861

(22) PCT Filed: Jul. 31, 2018

(86) PCT No.: PCT/US2018/044553
§ 371 (c)(1),
(2) Date: Jan. 31, 2020

(87) PCT Pub. No.: WO2019/027987
PCT Pub. Date: Feb. 7, 2019

(65) Prior Publication Data
US 2020/0291076 A1    Sep. 17, 2020

Related U.S. Application Data

(60) Provisional application No. 62/539,246, filed on Jul. 31, 2017.

(51) Int. Cl.
*C07K 14/435* (2006.01)
*C07K 14/705* (2006.01)
*C12N 15/86* (2006.01)
*G01N 33/50* (2006.01)

(52) U.S. Cl.
CPC ...... *C07K 14/435* (2013.01); *C07K 14/70596* (2013.01); *C12N 15/86* (2013.01); *G01N 33/5011* (2013.01); *G01N 33/5023* (2013.01); *C12N 2750/14143* (2013.01)

(58) Field of Classification Search
None
See application file for complete search history.

(56) References Cited

U.S. PATENT DOCUMENTS

| 4,554,101 A | 11/1985 | Hopp |
| 5,580,859 A | 12/1996 | Feigner |
| 5,679,647 A | 10/1997 | Carson |
| 5,703,055 A | 12/1997 | Feigner |

FOREIGN PATENT DOCUMENTS

| WO | WO 2017040526 | 3/2017 |
| WO | WO 2019027987 | 2/2019 |

OTHER PUBLICATIONS

Konishi et al. Mutation of a single allele of the cancer susceptibility gene BRCA1 leads to genomic instability in human breast epithelial cells, 2011, PNAS, 108, pp. 17773-17778. (Year: 2011).*
Bajaj et al., CD98-Mediated Adhesive Signaling Enables the Establishment and Propagation of Acute Myelogenous Leukemia. Cancer Cell. Nov. 14, 2016;30(5):792-805.
Dalton et al. SF3B1 mutations induce proteome remodeling, metabolic reprogramming, and a novel kind of tumor surface antigen in human cells [abstract]. In: Proceedings of the American Association for Cancer Research Annual Meeting 2018; Apr. 14-18, 2018; Chicago, IL. Philadelphia (PA): AACR; Cancer Res 2018;78(13 Suppl):Abstract nr 1408.
Darman et al., Cancer-Associated SF3B1 Hotspot Mutations Induce Cryptic 3' Splice Site Selection through Use of a Different Branch Point. Cell Rep. Nov. 3, 2015;13(5):1033-45.
Deboever et al., Transcriptome sequencing reveals potential mechanism of cryptic 3' splice site selection in SF3B1-mutated cancers. PLoS Comput Biol. Mar. 13, 2015;11(3).
Donnelly et al., DNA vaccines. Annu Rev Immunol. 1997;15:617-648.
Dvinge et al., RNA splicing factors as oncoproteins and tumour suppressors. Nat Rev Cancer. Jul. 2016;16(7):413-430.
Extended European Search Report issued for corresponding application No. 18840569.0 mailed Jun. 30, 2021, 16 pages.
Furney et al., SF3B1 mutations are associated with alternative splicing in uveal melanoma. Cancer Discov. Oct. 2013;3(10):1122-1129.
Gustin et al., Knockin of mutant PIK3CA activates multiple oncogenic pathways. Proc Natl Acad Sci U S A. Feb. 24, 2009;106(8):2835-2840.
Heagerty et al., Time-dependent ROC curves for censored survival data and a diagnostic marker. Biometrics. Jun. 2000;56(2):337-44.

(Continued)

*Primary Examiner* — Kara D Johnson
*Assistant Examiner* — Maytee Marie Contes De Jesus
(74) *Attorney, Agent, or Firm* — Casimir Jones, S.C.; Thomas A. Isenbarger

(57) ABSTRACT

The present disclosure relates to compositions and methods for treating cancers. In particular, the present disclosure provides materials and methods for identifying mis-splicing-associated surface antigens (MASAs) generated by altered spliceosome proteins, as well as materials and methods for targeting cancerous tumors expressing MASAs.

12 Claims, 16 Drawing Sheets

(56) References Cited

OTHER PUBLICATIONS

International Search Report issued for corresponding Int'l Application No. PCT/US2018/044553 mailed Mar. 22, 2019, 15 pages.
Kesarwani et al., Cancer-associated SF3B1 mutants recognize otherwise inaccessible cryptic 3' splice sites within RNA secondary structures. Oncogene. Feb. 23, 2017;36(8):1123-1133.
Kyte et al., A simple method for displaying the hydropathic character of a protein. J Mol Biol. May 5, 1982;157(1):105-32.
Palva et al., Secretion of interferon by Bacillus subtilis. Gene. May-Jun. 1983;22(2-3):229-235.
Madan et al., Aberrant splicing of U12-type introns is the hallmark of ZRSR2 mutant myelodysplastic syndrome, Nature Communications, 2015, vol. 6, No. 6042, 1-14.
Mohseni et al., MACROD2 overexpression mediates estrogen independent growth and tamoxifen resistance in breast cancers. Proc Natl Acad Sci U S A. Dec. 9, 2014;111(49):17606-17611.
Mosbach et al., Formation of proinsulin by immobilized Bacillus subtilis. Nature. Apr. 7, 1983;302(5908):543-545.
Prasad et al., Integrating transcriptomic and proteomic data for accurate assembly and annotation of genomes. Genome Res. Jan. 2017;27(1):133-144.
Thierry-Mieg et al., AceView: a comprehensive cDNA-supported gene and transcripts annotation. Genome Biol. 2006;7 Suppl 1(Suppl 1):S12.1-14.
Town et al., Exploring the surfaceome of Ewing sarcoma identifies a new and unique therapeutic target. Proc Natl Acad Sci U S A. Mar. 29, 2016;113(13):3603-3608.
The UniProt Consortium. UniProt: the universal protein knowledgebase. Nucleic Acids Res. Jan. 4, 2017;45(D1):D158-D169.
Wan et al., SF3B1 mutations in chronic lymphocytic leukemia, Blood, 2013 vol. 121 No. 23, 4627-4634.
Wu et al., Activation of diverse signaling pathways by oncogenic PIK3CA mutations. Nat Commun. Sep. 23, 2014;5:4961.
Zahari et al., Activating Mutations in PIK3CA Lead to Widespread Modulation of the Tyrosine Phosphoproteome. J Proteome Res. Sep. 4, 2015;14(9):3882-3891.

* cited by examiner

| Gene | AA change | Cancer type | | | | | | | Isogenic MCF-10A | | |
|---|---|---|---|---|---|---|---|---|---|---|---|
| | | BRCA | CLL | UVM | SKCM | MPM | MDS | unspec | Avg PSI K700E | Avg PSI WT | p-value |
| IL17RC | 8 AA ins | -# | | -# | -# | -# | -# | -# | 31.6 | 0 | 0.012 |
| PLXNB1 | 6 AA ins | -# | | -# | -# | | | -# | 15.2 | 1.7 | 0.0002 |
| BCAM | 21 AA del | -# | | -# | | | -# | | 12.5 | 0 | 0.36 |
| KIAA0319L | 5 AA ins | -# | -# | -# | -# | | | -# | 11.6 | 0 | 0.061 |
| SLC3A2 | 4 AA ins | -# | -# | -# | -# | -# | -# | -# | 11.4 | 0.33 | 5.89E-9# |
| LY75 | 6 AA ins | | -# | -# | | | | | 10 | 0.4 | 0.01 |
| NOMO1 | 6 AA ins | -# | | -# | | | | -# | 7.1 | 1.6 | 0.032 |
| ITFG3 | 6 AA ins | -# | | -# | -# | | -# | -# | 2.9 | 0 | 0.022 |
| TFRC | 6 AA ins | -# | | | -# | | -# | -# | 2.3 | 0 | 9.76E-5# |
| BSG | 16 AA del | | | -# | | | | -# | 1.2 | 0 | 0.001 |
| IGF1R | 8 AA ins | | | -# | | | | | 1.2 | 0 | 0.21 |
| IL6ST | 9 AA ins | | | | | | | -# | 0.4 | 0.1 | 0.29 |

FIG. 7

COMPOSITIONS AND METHODS FOR TARGETING MASAs TO TREAT CANCERS WITH SPLICEOSOME MUTATIONS

RELATED APPLICATIONS

This application is a national phase application under 35 U.S.C. § 371 of PCT International Application No.: PCT/US2018/044553, filed on Jul. 31, 2018, which claims priority to and the benefit of U.S. Provisional Patent Application No. 62/539,246 filed Jul. 31, 2017, the contents of each of which are incorporated herein by reference in its entirety for all purposes.

GOVERNMENT FUNDING

This invention was made with Government support under Federal Grant No. 125854 awarded by the Department of Defense. The Federal Government has certain rights to the invention.

FIELD

The present disclosure relates to compositions and methods for treating cancers. In particular, the present disclosure provides materials and methods for identifying mis-splicing-associated surface antigens (MASAs) generated by altered spliceosome proteins, as well as materials and methods for targeting cancerous tumors expressing MASAs.

BACKGROUND

Worldwide each year, more than 15 million people are diagnosed with cancer, and 8 million patients die of the disease. A seminal success of targeted cancer therapy was the 1998 approval of trastuzumab for HER2 positive breast cancer. Since then, no drug specific for a different genetic alteration in breast cancer has been approved, even while the catalog of breast cancer mutations has expanded. This is partly due to the fact that most cancer mutations occur in only a few percent of cases, complicating prioritization of research and incentives for clinical trials. There is an unmet need to find new drivers of cancer that can be therapeutically targeted for a variety of cancers.

SUMMARY

Embodiments of the present disclosure include a method of identifying a mis-splicing-associated surface antigen (MASA). In accordance with these embodiments, the method includes engineering an isogenic cell line to express a spliceosome protein comprising at least one mutation and identifying at least one mRNA comprising a cryptic splice site in the isogenic cell line, wherein the least one mRNA comprising the cryptic splice site is enriched in the isogenic cell line compared to a parental cell line.

In some embodiments, the method further includes identifying at least one MASA polypeptide from a protein encoded by the at least one mRNA comprising the cryptic splice site, wherein the protein is generated by virtue of activity of the mutated spliceosome protein. In some embodiments, the spliceosome protein is selected from SF3B1, U2AF1, SRSF2, ZRSR2, RBM10, FUBP1, and any derivatives or variations thereof. In some embodiments, the spliceosome protein is SF3B1 and any derivatives or variations thereof. In some embodiments, the spliceosome protein is SF3B1, and the at least one mutation alters an amino acid at position E622, Y623, R625, N626, W658, H662, T663, K666, Q698, Q699, K700, V701, R702, 1704, S705, A706, G740, K741, G742, R775, E776, D781, M784, K785, 1787, D894, E902, or a combination thereof. In some embodiments, the spliceosome protein is SF3B1, and the at least one mutation produces one of the following amino acid substitutions: E622Q, N626D, K666E, K666Q, K700E, and D781E, or a combination thereof. In some embodiments, the spliceosome protein is SF3B1, and the at least one mutation produces amino acid substitution K700E. In some embodiments, the mutation includes an in-frame insertion or an in-frame deletion.

In some embodiments, the at least one mRNA comprising the cryptic splice site is selected from CD98 (SLC3A2), BCAM, BSG, IL17RC, IL6ST, ITFG3, KIAA0319L, LY75, NOM01, PLXNB1, TFRC, IGFR1, and IL6ST. In some embodiments, the method further includes identifying at least one MASA on a protein encoded by the at least one mRNA selected from CD98 (SLC3A2), BCAM, BSG, IL17RC, IL6ST, ITFG3, KIAA0319L, LY75, NOM01, PLXNB1, TFRC, IGFR1, and IL6ST. In some embodiments, the isogenic cell line is selected from a mammalian cell line, a non-mammalian cell line, a human cell line, a primary human cell line, a transformed cell line, a transformed human cell line, cancerous cell line, a primary tumor cell line, and a breast cancer epithelial cell line. In some embodiments, the isogenic cell line is selected from MCF-10A cells, hTERT cells, hTERT-IMEC cells, and Mel202 uveal melanoma cells.

Embodiments of the present disclosure also include a construct for expressing the spliceosome protein of any of above embodiments, a construct for expressing the at least one mRNA comprising the cryptic splice site of any of above embodiments, and a construct for expressing the at least one MASA polypeptide of any of above embodiments.

Embodiments of the present disclosure also include an isogenic cell line engineered to express a spliceosome protein comprising at least one mutation, wherein the isogenic cell line is enriched for at least one mRNA comprising a cryptic splice site as compared to a parental cell line due to expression of the mutated spliceosome protein.

In some embodiments, the at least one mRNA comprising the cryptic splice site encodes for a protein comprising a mis-splicing-associated surface antigen (MASA) polypeptide. In some embodiments, the spliceosome protein is selected from SF3B1, U2AF1, SRSF2, ZRSR2, SF3A1, U2AF2, and any derivatives or variations thereof. In some embodiments, the spliceosome protein is SF3B1, and the at least one mutation alters an amino acid at position E622, Y623, R625, N626, W658, H662, T663, K666, Q698, Q699, K700, V701, R702, 1704, S705, A706, G740, K741, G742, R775, E776, D781, M784, K785, 1787, D894, E902, or a combination thereof. In some embodiments, the at least one mRNA comprising the cryptic splice site is selected from CD98 (SLC3A2), BCAM, BSG, IL17RC, IL6ST, ITFG3, KIAA0319L, LY75, NOM01, PLXNB1, TFRC, IGFR1, and IL6ST. In some embodiments, the isogenic cell line is selected from a mammalian cell line, a non-mammalian cell line, a human cell line, a primary human cell line, a transformed cell line, a transformed human cell line, cancerous cell line, a primary tumor cell line, and a breast cancer epithelial cell line. In some embodiments, the isogenic cell line is selected from MCF-10A cells, hTERT cells, hTERT-IMEC cells, and Mel202 uveal melanoma cells.

Embodiments of the present disclosure include a method for identifying a modulating agent of a mis-splicing-associated surface antigen (MASA). In accordance with these embodiments, the method includes engineering an isogenic cell line to express a spliceosome protein comprising at least one mutation, wherein the isogenic cell line is enriched for a protein comprising at least one MASA polypeptide as compared to a parental cell line due to expression of the mutated spliceosome protein, isolating the protein comprising the at least one MASA polypeptide, and screening a plurality of modulating agents for binding to the at least one MASA polypeptide.

In some embodiments, the plurality of modulating agents includes one or more of an antibody, a polyclonal antibody, a monoclonal antibody, single-chain variable fragment, a bi-specific antibody, or an antigen binding fragment thereof.

The disclosure provides for other aspects and embodiments that will be apparent in light of the following detailed description and accompanying figures.

BRIEF DESCRIPTION OF THE DRAWINGS

(FIG. 2A) In-frame changes are predicted to make abnormal protein, while frameshifts make PTCs and cause degradation by NMD. (FIG. 2B) Examples of mis-splicing outcomes in known cancer genes, identified through publicly available RNA-seq data.

(FIG. 5A) Enrichment of cryptic CD98 protein in SF3B1-mutant MCF-10A cells. MS/MS spectra of the cryptic peptide in mutant (K700E-1 and -2) versus targeted wild type (TWT-1) control cells. (FIG. 5B) Quantification of protein abundance values.

FIG. 7. Predicted MASAs. AA=amino acid, BRCA=breast cancer, CLL—chronic lymphocytic leukemia, UVM=uveal melanoma, SKCM=skin cutaneous melanoma, MPM=malignant pleural mesothelioma, MDS=myelodysplastic syndrome, unspec=unspecified in study, PSI=percent spliced in.

(FIG. 11A) Mutant or control adeno-associated viruses were used to create heterozygous knockins of K700E, R702R, or targeted wild type (TWT) in hTER-IMEC cells. (FIG. 11B) One K700E and five control hTERT-IMEC clones were genotyped by Sanger sequencing.

(FIG. 12A) Targeting approach for mutation inactivation in Mel202 cells. Shaded rectangle indicates lack of transcription of the targeted allele. (FIG. 12B) Sanger sequencing confirmation of mutation inactivation. Cor=corrected, Ran=random integrant control.

DETAILED DESCRIPTION

Figure 1:
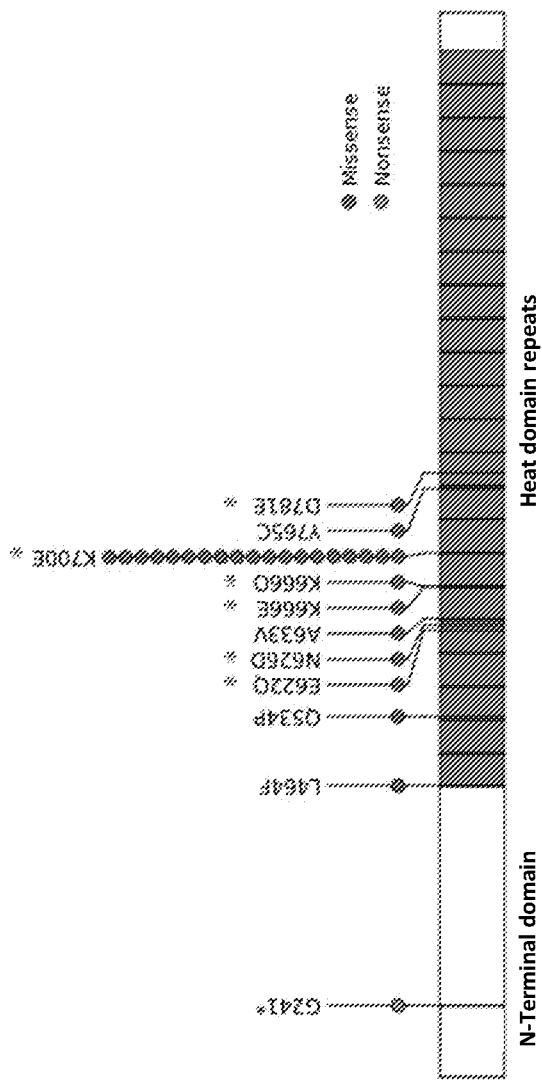
FIG. 1. Spectrum of SF3B1 mutations in breast cancer. Red asterisks indicate mutations which are hotspots in other cancer types. Data are pooled from Cosmic and cBioportal databases.

Described herein are inhibitors of mis-splicing-associated surface antigen (MASAs) polypeptides, and their use in treating cancer. Mutant spliceosome proteins can cause mis-splicing of RNA in thousands of genes and often drives or results in cancer. A group of these mis-spliced genes are termed herein as MASAs. The MASA may be a cell surface antigen or transmembrane protein that can be targeted to treat cancer. MASA inhibitors may be administered to a subject to treat cancer.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The term "cancer" refers to any disease in which a group of cells displays uncontrolled growth/proliferation. Cancer cells tend to invade surrounding tissue and metastasize to new body sites. A "tumor" refers to an abnormal growth of cells or tissues, including both benign and malignant types of cells/tissues. A benign or malignant tumor may be comprised of at least one cell and/or tissue and may be cancerous or precancerous. Cancers may include, for example, lung cancer, breast cancer, pancreatic cancer, leukemia, melanoma, mesothelioma, hepatocellular carcinoma, adenoid cystic carcinoma, ampullary carcinoma, bladder carcinoma, prostate carcinoma, renal cell carcinoma, thymoma, medulloblastoma, myelodysplastic syndrome, acute myeloid leukemia, bladder carcinoma, cervical carcinoma, lung adenocarcinoma, pancreas adenocarcinoma, uterine carcinoma, myelodysplastic syndrome, and acute myeloid leukemia. Leukemia may include, for example, chronic lymphocytic leukemia, myelodysplastic syndrome, and acute myeloid leukemia. In some embodiments, cancer associated with SF3B1 mutations includes lung cancer, breast cancer, pancreatic cancer, leukemia, melanoma, mesothelioma, hepatocellular carcinoma, adenoid cystic carcinoma, ampullary carcinoma, bladder carcinoma, prostate carcinoma, renal cell carcinoma, thymoma, or medulloblastoma. In some embodiments, cancer associated with U2AF1 mutations includes myelodysplastic syndrome, acute myeloid leukemia, bladder carcinoma, cervical carcinoma, lung adenocarcinoma, pancreas adenocarcinoma, or uterine carcinoma.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, TX; SAS Institute Inc., Cary, NC.). The healthy or normal levels or ranges for a target or for a protein activity may be defined in accordance with standard practice. A control may be an agent or cell without cancer. A control may be a molecule, or sample comprising a molecule, with a polypeptide or polymer, that is different from a MASA inhibitor as detailed herein. A control may be a subject, or a sample therefrom, whose disease state is known. The subject, or sample therefrom, may be healthy, diseased, diseased prior to treatment, diseased during treatment, or diseased after treatment, or a combination thereof. The control may include, for example, an agent or cell alone or by itself.

The term "expression vector" indicates a plasmid, a virus or another medium, known in the art, into which a polynucleotide sequence for encoding a desired protein can be inserted or introduced.

The term "host cell" is a cell that is susceptible to transformation, transfection, transduction, conjugation, and the like with a nucleic acid construct or expression vector. Host cells can be derived from plants, bacteria, yeast, fungi, insects, animals, etc. In some embodiments, the host cell includes *Escherichia coli*.

The terms "inhibit" or "inhibiting" mean that an activity is decreased or prevented in the presence of an inhibitor as opposed to in the absence of the inhibitor. The term "inhibition" refers to the reduction or down regulation of a process or the elimination of a stimulus for a process, which results in the absence or minimization of the expression or activity of a polypeptide or antigen or disease. Inhibition may be direct or indirect. Inhibition may be specific, that is, the inhibitor inhibits the polypeptide or antigen and not others.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three-dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids. A domain may be comprised of a series of the same type of motif.

"Recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed, or not expressed at all.

"Sample" or "test sample" as used herein can mean any sample in which the presence and/or level of a target is to be detected or determined or any sample comprising an agent, cell, MASA, or MASA inhibitor as described herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Subject" as used herein can mean a mammal that wants or is in need of the herein described MASA inhibitors. The subject may be a patient. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

"Substantially identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids.

"Treatment" or "treating," when referring to protection of a subject from a disease, means preventing, suppressing, repressing, ameliorating, or completely eliminating the disease. Preventing the disease involves administering a composition of the present invention to a subject prior to onset of the disease. Suppressing the disease involves administering a composition of the present invention to a subject after induction of the disease but before its clinical appearance. Repressing or ameliorating the disease involves administering a composition of the present invention to a subject after clinical appearance of the disease.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequence substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Bioi.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Spliceosome

Mutant spliceosome-induced mis-splicing of RNA can drive cancer phenotypes, create cell surface antigens that can be targeted with immunotherapeutic reagents, and produce vulnerabilities that can be therapeutically exploited. A spliceosome is a large and complex molecular machine found primarily within the cell nucleus of eukaryotic cells. The spliceosome comprises small nuclear RNAs (snRNAs) and proteins. The snRNAs that make up the major spliceosome are named U 1, U2, U4, US, and U6, and they participate in several RNA-RNA and RNA-protein interactions. The spliceosome removes introns from a transcribed pre-mRNA, a type of primary transcript. This process is generally referred to as splicing. Only eukaryotes have spliceosomes, and some organisms have a second spliceosome called the minor spliceosome. Spliceosome proteins include, for example, SF3B1, U2AF1, SRSF2, ZRSR2, RBM10, and FUBP1. In some embodiments, the spliceosome protein comprises SF3B1 and any derivatives of variations thereof. SF3B1 is a spliceosome protein that is recurrently mutated in various cancers. The SF3B1 mutations may be heterozygous missense substitutions. Mutant SF3B1 may mis-splice mRNA through cryptic 3' splice site selection. The SF3B1 spliceosome protein may comprise a mutation at an amino acid selected from E622, Y623, R625, N626, W658, H662, T663, K666, Q698, Q699, K700, V701, R702, 1704, S705, A706, G740, K741, G742, R775, E776, D781, M784, K785, 1787, D894, E902, or a combination thereof. The SF3B1 spliceosome protein may comprise at least one amino acid substitution selected from L464F, Q534P, E622Q, N6260, A633V, K666E, K666Q, K700E, Y765C, and D781E, or a combination thereof (FIG. 1). In some embodiments, the SF3B1 spliceosome protein includes at least one amino acid substitution selected from E622Q, N6260, K666E, K666Q, K700E, and D781E, or a combination thereof. In some embodiments, the amino acid substitution in SF3B1 is K700E.

Figure 2:
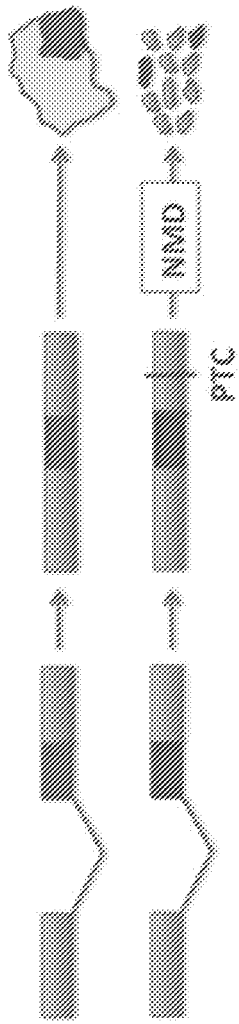
FIG. 2A and FIG. 2B. Potential outcomes of mSF3B1 mis-splicing.
Figure 3:
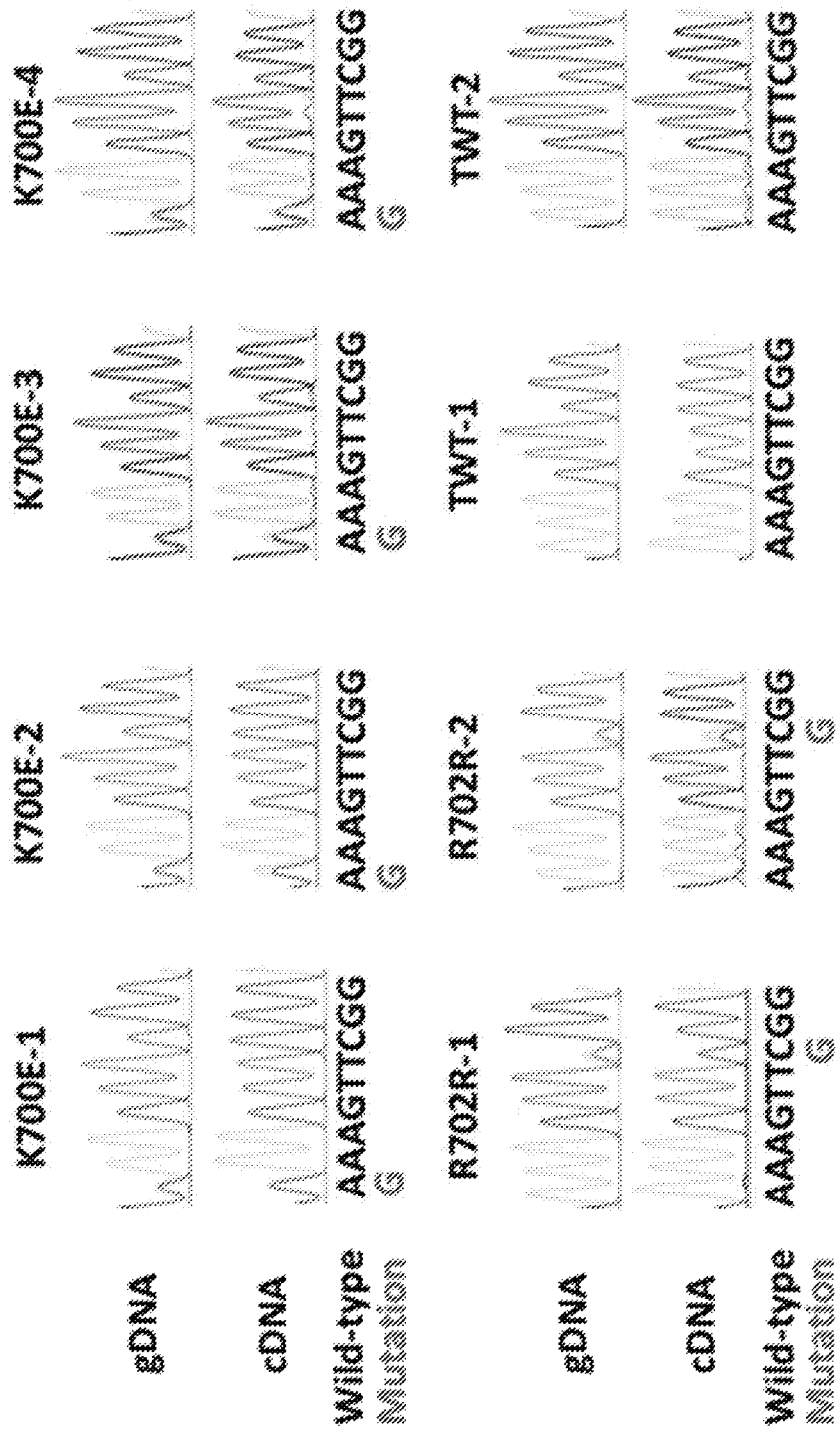
FIG. 3. Heterozygous mSF3B1 knockins in MCF-10A cells. Four clones of the predominant K700E hotspot mutation, as well as control clones with either a silent substitution that is a human SNP (R702R) or "targeted wild-type" (TWT), were obtained using gene targeting.

Mutant spliceosome proteins may cause mis-splicing of RNA in a gene, including known cancer genes (FIG. 2). The mis-splicing may result in premature truncation codons (PTCs) that trigger nonsense-mediated mRNA decay (NMD). The mis-splicing may result in in-frame mutations that result in mutant proteins. The NMD pathway is a quality control mechanism that may be protective to spliceosome-mutant cells, as proteins that would otherwise be made from hundreds of frameshifted RNAs would be highly abnormal and potentially toxic.

In accordance with these embodiments, other spliceosome proteins and/or splicing factors can, when altered, lead to the generation of MASAs that can be therapeutic targets for various cancer therapies. For example, spliceosome proteins can include, but are not limited to, AGGF1 (UniProt No. Q8N302), C9orf78 (UniProt No. Q9NZ63), CCARI (UniProt No. Q8IX12), CD2BP2 (UniProt No. O95400), CDC5L (UniProt No. Q99459), CDK11A (UniProt No. Q9UQ88), CDK12 (UniProt No. Q9NYV4), CELF4 (UniProt No. Q9BZC1), CFAP20 (UniProt No. Q9Y6A4), CLK4 (UniProt No. Q9HAZ1), CWC22 (UniProt No. Q9HCG8), DDX17 (UniProt No. Q92841), DDX18 (UniProt No. Q9NVP1), DDX20 (UniProt No. Q9UHI6), DDX23 (UniProt No. Q9BUQ8), DDX26B (UniProt No. Q5JSJ4), DDX27 (UniProt No. Q96GQ7), DDX3X (UniProt No. O00571), DDX41 (UniProt No. Q9UJV9), DDX5 (UniProt No. P17844), DDX50 (UniProt No. Q9BQ39), DHX16 (UniProt No. O60231), DHX35 (UniProt No. Q9H5Z1), DHX36 (UniProt No. Q9H2U1), DHX9 (UniProt No. Q08211), EEF1A1 (UniProt No. 68104), EFTUD2 (UniProt No. Q15029), EIF2S2 (UniProt No. P20042), ELAVL1 (UniProt No. Q1JQ73), ELAVL2 (UniProt No. Q91903), ELAVL4 (UniProt No. P26378), FAM58A (UniProt No. Q8NIB3), FRA10AC1 (UniProt No. Q70Z53), FUBP1 (UniProt No. Q96AE4), FUBP3 (UniProt No. Q96124), GPATCH8 (UniProt No. Q9UKJ3), HNRNPCLI (UniProt No. O60812), HNRNPD (UniProt No. Q14103), HNRNPDL (UniProt No. O14979), HNRNPH3 (UniProt No. P31942), HNRNPK (UniProt No. P61978), HNRNPL (UniProt No. P14866), IGF2BP3 (UniProt No. O00425), INTS4 (UniProt No. Q96HW7), INTS7 (UniProt No. Q9NVH2), KIAA1429 (UniProt No. Q69YN4), KIN (UniProt No. O60870), MBNL2 (UniProt No. Q5VZF2), MOV10 (UniProt No. Q9HCE1), NCBP1 (UniProt No. Q09161), NELFE (UniProt No. P18615), NOVA1 (UniProt No. P51513), NSRP1 (UniProt No. Q9H0G5), PABPC1 (UniProt No. P11940), PCBP1 (UniProt No. Q15365), PCBP2 (UniProt No. Q15366), PCBP3 (UniProt No. P57721), PHF5A (UniProt No. Q7RTV0), PLRGI (UniProt No. O43660), PPIG (UniProt No. Q13427), PPILI (UniProt No. Q9Y3C6), PPIL4 (UniProt No. Q8WUA2), PRPF3 (UniProt No. O43395), PRPF38B (UniProt No. Q5VTL8), PRPF39 (UniProt No. Q86UA1), PRPF40B (UniProt No. Q6NWY9), PRPF4B (UniProt No. Q13523), PSIPI (UniProt No. O75475), QKI (UniProt No. Q9QYS9), RALYL (UniProt No. Q86SE5), RBBP6 (UniProt No. Q7Z6E9), RBM10 (UniProt No. P98175), RBM15B (UniProt No. Q8NDT2), RBM25 (UniProt No. P49756), RBM26 (UniProt No. Q5T8P6), RBM27 (UniProt No. Q5SFM8), RBM7 (UniProt No. Q9Y580), RBM8A (UniProt No. Q9Y5S9), RBMX (UniProt No. P38159), RBMX2 (UniProt No. Q9Y388), RNF20 (UniProt No. Q5VTR2), SF1 (UniProt No. Q13285), SF3B1 (UniProt No. O75533), SF3B2 (UniProt No. Q13435), SF3B3 (UniProt No. Q15393), SKIV2L2 (UniProt No. P42285), SNRNP200 (UniProt No. O75643), SNRNP35 (UniProt No. Q16560), SNRNP48 (UniProt No. Q6IEG0), SNRPD3 (UniProt No. P62318), SNRPN (UniProt No. P63162), SPEN (UniProt No. Q96T58), SRSF2 (UniProt No. Q01130), SRSF5 (UniProt No. Q13243), SYNCRIP (UniProt No. O60506), TCERGI (UniProt No. O14776), THOC5 (UniProt No. Q13769), THOC6 (UniProt No. Q86W42), THOC7 (UniProt No. Q619Y2), THRAP3 (UniProt No. Q9Y2W1), TIAl (UniProt No. P31483), TIALI (UniProt No. Q01085), TNPO1 (UniProt No. Q92973), TRIM24 (UniProt No. O15164), TTC14 (UniProt No. Q96N46), U2AF1 (UniProt No. Q8WU68), U2AF2 (UniProt No. P26368), U2SURP (UniProt No. O15042), WBP11 (UniProt No. Q9Y2W2), WBP4 (UniProt No. O75554), ZC3H13 (UniProt No. Q5T200), ZC3H18 (UniProt No. Q86VM9), ZC3H4 (UniProt No. Q9UPT8), ZCCHC8 (UniProt No. Q6NZY4), ZCRB1 (UniProt No. Q8TBF4), ZMYM3 (UniProt No. Q14202), ZNF131 (UniProt No. P52739), ZNF207 (UniProt No. O43670), ZRSR2 (UniProt No. Q15696).

3. Mis-Splicing-Associated Surface Antigens (MASAs)

MASA polypeptides include cell surface antigens and/or transmembrane proteins comprising at least one amino acid substitution relative to wild-type, wherein the amino acid substitution results from mis-splicing of a target mRNA molecule by a spliceosome protein comprising at least one mutation. The amino acid substation in the MASA polypeptide may be the result of an in-frame insertion or in-frame deletion in the corresponding mRNA molecule. In some cases, the MASA is associated with, or results in a cancerous tumor.

MASAs of the present disclosure can arise from any mRNA molecule that is mis-spliced (e.g., due to the presence of a cryptic splice site) by an altered or mutated spliceosome protein. In some embodiments, the mis-spliced mRNA molecules encode any of the following MASA polypeptides: CD98 (SLC3A2), BCAM, BSG, IL17RC, IL6ST, ITFG3, KIAA0319L, LY75, NOM01, PLXNB1, TFRC, IGFR1, and IL6ST. In some embodiments, the MASA polypeptide includes a cell surface antigen. In some embodiments, the MASA polypeptide includes a transmembrane protein. In some embodiments, the MASA polypeptide comprises an extracellular domain. The MASA polypeptide may include a mutation in the extracellular domain. MASA polypeptides include, but are not limited to, C098 (SLC3A2), BCAM, BSG, IL17RC, IL6ST, ITFG3, KIAA0319L, LY75, NOM01, PLXNB1, TFRC, IGFR1, and IL6ST.

a. Method of Identifying a MASA Polypeptide

Embodiments of the present disclosure include methods for identifying a MASA. In accordance with these embodiments, the method includes engineering a cell line to express a spliceosome protein that has been genetically altered in some way, such that the splicing function of the altered spliceosome protein generates a mis-spliced mRNA molecule. Once translated into a protein, the mis-spliced mRNA molecule can give rise to a MASA, as described further herein. In some embodiments, genetic alterations in the spliceosome protein can include, but are not limited to, missense mutations, point mutations, in-frame insertions, in-frame deletions, and the like. Standard techniques for engineering a cell line to express a mutated spliceosome protein are well known in the art, including the generation of isogenic cell lines from parental cell lines.

For example, an isogenic cell line includes a cell line that has been engineered from a parental cell line through the introduction of a targeted gene mutation, such as a mutation in a spliceosome protein. In doing so, the parental cell line can be used as a control line to which the engineered line can be referenced and compared. Isogenic cell line pairs can be used as a basis to identify a MASA generated by the mutated spliceosome protein, as well as to generate antibodies to the MASA itself. As described further herein, a mutated spliceosome protein can act on a cryptic splice site in an mRNA molecule in an isogenic cell line, such that a MASA is produced only in that isogenic cell line and not in the parental cell line. Therefore, embodiments of the present disclosure include identifying at least one mRNA that includes a cryptic splice site in the isogenic cell line, due to the enrichment of the mRNA comprising the cryptic splice site in the isogenic cell line compared to a parental cell line. Isogenic and parental cell lines can be any cell line that is amenable to genetic engineering and laboratory manipulation/culturing, including, but not limited to, a mammalian cell line, a non-mammalian cell line, a human cell line, a primary human cell line, a transformed cell line, a transformed human cell line, cancerous cell line, a primary tumor cell line, and a breast cancer epithelial cell line. In some embodiments, the isogenic cell line includes MCF-10A cells, hTERT cells, hTERT-IMEC cells, or Mel202 uveal melanoma cells.

Embodiments of the present disclosure also include constructs for expressing a mutated spliceosome protein in an isogenic cell line, as well as constructs for expressing a MASA polypeptide or the corresponding mis-spliced mRNA that encodes the MASA polypeptide. Examples of such constructs are known in the art and include those depicted in FIG. 14.

b. MASA Inhibitors

Further provided herein is an agent that inhibits a MASA polypeptide. The MASA inhibitor may comprise a small molecule, a carbohydrate, an inhibitory RNA, an antibody, or a combination thereof. In some embodiments, the MASA inhibitor comprises an antibody. In some embodiments, the inhibitor comprises a polynucleotide. In some embodiments, the MASA inhibitor comprises a bispecific antibody. In some embodiments, the MASA inhibitor comprises adoptive T cells.

In some embodiments, the inhibitor comprises a polypeptide. In some embodiments, the polypeptide comprises an antibody. Further provided are polynucleotides encoding the inhibitor detailed herein. A vector may include the polynucleotide encoding the inhibitor detailed herein. To obtain expression of a polypeptide, one may subclone the polynucleotide encoding the polypeptide into an expression vector that contains a promoter to direct transcription, a transcription/translation terminator, and if for a nucleic acid encoding a protein, a ribosome binding site for translational initiation. An example of a vector is pet24. Suitable bacterial promoters are well known in the art. Further provided is a host cell transformed or transfected with an expression vector comprising a polynucleotide encoding an inhibitor as detailed herein. Bacterial expression systems for expressing the protein are available in, e.g., *E. coli, Bacillus* sp., and Salmonella (Paiva et al., Gene 1983, 22, 229-235; Mosbach et al., Nature 1983, 302, 543-545). Kits for such expression systems are commercially available. Eukaryotic expression systems for mammalian cells, yeast, and insect cells are well known in the art and are also commercially available. Retroviral expression systems can be used in the present invention.

The inhibitor may be expressed recombinantly in a host cell according to one of skill in the art. The inhibitor may be purified by any means known to one of skill in the art. For example, the inhibitor may be purified using chromatography, such as liquid chromatography, size exclusion chromatography, or affinity chromatography, or a combination thereof.

Embodiments of the present disclosure also include methods for identifying a modulating agent of a MASA. In accordance with these embodiments, the method includes engineering an isogenic cell line to express a spliceosome protein comprising at least one mutation, as described further herein. Due to the expression of the mutated spliceosome protein, the isogenic cell line is enriched for a protein comprising at least one MASA polypeptide as compared to a parental cell line. The MASA polypeptide(s) can then be isolated and subject to a screen that includes exposing the MASAs to candidate agents that may bind to and modulate the MASAs. Such candidate MASA modulating agents can be further tested for therapeutic efficacy and specificity in the context of cancer immunotherapy. For example, in some embodiments, the MASA modulating agent can be an antibody, a polyclonal antibody, a monoclonal antibody, single-chain variable fragment, a bi-specific antibody, or an antigen binding fragment thereof, that binds and/or modulates one or more aspects of the MASA. In some cases, the MASA modulating agent can be used as a means for identifying a cancer cell/tumor, and/or the MASA modulating agent can be used to target a cancer cell/tumor and deliver one or more therapeutic agents to the cancer cell/tumor.

4. Administration

The term "administration" or "administering," as used herein, refers to providing, contacting, and/or delivery of an agent or an inhibitor by any appropriate route to achieve the desired effect. An agent or inhibitor may be comprised in a composition for administration. A composition may comprise the MASA inhibitor.

The MASA inhibitor as detailed above can be formulated into a composition in accordance with standard techniques well known to those skilled in the pharmaceutical art. The composition may be prepared for administration to a subject. Such compositions comprising a MASA inhibitor can be administered in dosages and by techniques well known to those skilled in the medical arts taking into consideration such factors as the age, sex, weight, and condition of the particular subject, and the route of administration.

The MASA inhibitor can be administered prophylactically or therapeutically. In prophylactic administration, the MASA inhibitor can be administered in an amount sufficient to induce a response. In therapeutic applications, the MASA inhibitor is administered to a subject in need thereof in an amount sufficient to elicit a therapeutic effect. An amount adequate to accomplish this is defined as "therapeutically effective dose." Amounts effective for this use will depend on, e.g., the particular composition of the MASA inhibitor regimen administered, the manner of administration, the stage and severity of the disease, the general state of health of the patient, and the judgment of the prescribing physician.

The MASA inhibitor can be administered by methods well known in the art as described in Donnelly et al. (Ann. Rev. Immunol. 1997, 15, 617-648); Feigner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The MASA inhibitor can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The MASA inhibitor can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the POP is administered intravenously, intraarterially, or intraperitoneally to the subject.

5. Methods of Treating Cancer in a Subject

MASAs may be targeted with inhibitors such as immunotherapeutics to treat cancer. Provided herein are methods of treating cancer in a subject. The methods may include administering to the subject a composition comprising a MASA polypeptide inhibitor as detailed herein. In some embodiments, the method further comprises co-administering to the subject an agent that inhibits a spliceosome protein as detailed herein. In some embodiments, the method further comprises co-administering to the subject a PTC readthrough drug. In some embodiments, the cancer comprises a solid tumor. In some embodiments, the cancer comprises a hematologic malignancy. In some embodiments, the cancer comprises lung cancer, breast cancer, pancreatic cancer, leukemia, melanoma, or mesothelioma.

6. Examples

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Materials and Methods

Cell Culture. The non-transformed human breast epithelial cell line MCF-10A was obtained from ATCC and maintained in DMEM/F12 (1:1) supplemented with 5% horse serum (Life Technologies), 20 ng/ml EGF (Sigma-Aldrich), 10 µg/mL insulin (Life Technologies), 0.5 µg/mL hydrocortisone (Sigma-Aldrich), and 0.1 µg/mL cholera toxin (Sigma-Aldrich). All gene targeted derivatives of MCF-10A were maintained in the same media, except PIK3CA E545K knockins, which were maintained without EGF (Gustin, J. et al. PNAS 2009, 106, 2835-2840). Telomerase-immortalized human mammary epithelial cells (hTERT-IMEC) were a gift from J W Shay and were maintained in the same media as MCF-10A except horse serum was substituted with 2% charcoal dextran-stripped FBS (Life Technologies). Mel202 uveal melanoma cells were obtained from Sigma-Aldrich and maintained in RPMI with 20% FBS (Life Technologies). HNT34 acute myeloid leukemia cells were obtained from DSMZ and maintained in RPMI with 10% FBS. KG-1 acute myeloid leukemia cells were a gift from RA Casero and maintained in RPMI with 10% FBS. Pane 05.04 pancreatic adenocarcinoma cells were a gift from J R Eshleman and maintained in DMEM, 10% FBS, and 10 µg/mL insulin. PANC-1 pancreatic adenocarcinoma cells were a gift from M Goggins and maintained in DMEM with 10% FBS. HEK-293T cells were obtained from ATCC and maintained in DMEM with 10% FBS.

Patient Samples. Patients with SF3B1-mutant acute myeloid leukemia were identified via the Johns Hopkins Molecular Pathology Next Gen Sequencing Core, a CLIA-certified laboratory using cancer gene panels with either the Illumina or ION TORRENT NGS platforms. Patient consent was obtained for sample collection under a Johns Hopkins IRS-approved study. Ten milliliters of peripheral blood per patient were withdrawn in EDT A-containing tubes, erythrocytes were lysed with ACK lysing buffer (Quality Biological), leukocytes were centrifuged, and RNA was isolated from cell pellets using RNEASY/QIASHREDDER kits (Qiagen). Single-stranded eDNA was generated using First Strand eDNA Synthesis Kit (Amersham Biosciences).

Gene Targeting. Gene targeting was carried out using recombinant AAV technology (Gustin, J. et al. PNAS 2009, 106, 2835-2840). AAV vectors targeting SF3B1 were produced by ligating wild type homology arms generated by PCR into an AAV plasmid backbone (Agilent, La Jolla, CA), followed by site-directed mutagenesis by overlap extension PCR to generate the K700E and R702R alterations. Infectious virus was prepared by co-transfecting HEK-293T cells with pHelper, pRC (Agilent) and the respective SF3B1 mutation-carrying rAAV targeting plasmids. Cell lines were then infected with AAV, and single G418-resistant clones were isolated and assayed for integration of the targeting cassette. For Mel202 cells, which contain one copy of SF3B1$^{R625G}$ and two copies of WT SF3B1, gene targeting was stopped at this step, and clones in which the targeting cassette integrated into- and inactivated-the mutant allele were used for functional studies, with controls provided by G418-resistant clones in which the targeting cassette integrated randomly into the genome. For MCF-10A and hTERT-IMEC cells, targeted clones were next exposed to Cre-expressing recombinant adenovirus to remove the neomycin cassette as previously described (Gustin, J. et al. PNAS 2009, 106, 2835-2840). All clones were subjected to confirmation by Sanger sequencing of genomic DNA and eDNA to ensure each clone harbored and expressed the intended mutation. Primer sequences for homology arm construction, mutagenesis, pre-Cre PCR screening, post-Cre PCR screening, genomic DNA sequencing, and eDNA sequencing are available upon request.

10074| RNA-seq Analysis. Total RNA was harvested from cultured cell pellets as per above for patient samples, and RNA-seq libraries were constructed using the Illumina TRUSEQ RNA Sample Preparation Kit v3 as described previously (Prasad, T. S. et al. Genome Res. 2017, 27, 133-144). The clusters generated from the final library were sequenced on an Illumina HISCAN SQ system to obtain a total of approximately 40 million paired-end reads of 101 base pairs in length per replicate. Reads were aligned using Bowtie 2 (Version 2.1.0) against the GRCh38/hg38 version of the human genome, and assembly was done with the Top Hat (Version 2.0.1 0) and Cufflinks pipeline. FPKM for transcripts were obtained with StringTie and CuffDiff, and differential isoform- and gene-level mRNA expression between mutant and control cells were analyzed with DESeq2. Splice junctions were identified and quantified using DEXseq, and "percent spliced in" (PSI) values for junctions were determined by dividing the read counts for a given junction by all read counts that include either the donor or acceptor site (for alternate acceptors or donors, respectively). Differences in PSI between mutant and control cells were tested for significance using a moderated t-test with p-value≤0.05 and Benjamini-Hochberg q-value≤ 0.1. Novel junctions were those not found in the major transcriptome databases KnownGene (Hsu, F. et al. Bioinformatics 2006, 22, 1036-1046), AceView (Thierry-Mieg, D. & Thierry-Mieg, J. Genome Bioi. 2006, 7 Suppl 1, S12.1-14), and Ensembl (Aken, B. L. et al. Nucleic Acids Res. 2017, 45, D635-D642).

PCR Validation of Aberrant Splice Junctions. Endpoint PCR was performed on eDNA from patient samples and cell lines using primers designed to amplify both the cryptic junction of interest and its paired canonical junction, so that both isoforms can be amplified in the same PCR reaction. To reduce nonspecific amplification of residual genomic DNA, at least one primer overlapped an exon-exon junction adjacent to the splice junction of interest. All primer sequences are available upon request.

SILAC Proteomic Analysis. SILAC-based mass spectrometry of MCF-10A cells was performed as previously described (Wu, X. et al. Nature Communications 2014, 5, 4961). Briefly, two independent K700E clones and a TWT clone were propagated for >7 population doublings in DMEM/F12 SILAC media with complete supplements, but deficient in both L-lysine and L-arginine (Thermo Fisher Scientific) and supplemented with light lysine (K) and arginine (R) for light, $^2H_4$-K and $^{13}C_6$-R for medium state, and $^{13}C^1{}_6{}_5N_2$-K and $^{13}C^1{}_6{}_5N_4$-R for heavy state labelling (Cambridge Isotope Laboratories). Cells were lysed, equal protein amounts of the three SILAC-labelled states were mixed, and overnight digestion with trypsin was performed. Peptides were then subjected to liquid chromatography-tandem mass spectrometry (LC-MS/MS) analysis using a reverse-phase LC system interfaced with an L TQ-Orbitrap Velos mass spectrometer (Thermo Fisher Scientific). Proteome Discoverer (Version 1.4.1.14; Thermo Fisher Scientific) suite was used for quantification and database searches of both known and novel peptides, the latter using a custom, three-frame-translated genome search workflow.

In Silico Identification of Candidate MASAs. Potential MASA-encoding splice junctions were identified from RNA-seq data sets of junctions upregulated in SF3B1-mutant cells, gathered both from isogenic MCF-10A cells and published analyses of human tumors and cell models. The junctions were first filtered to include those not annotated in transcriptome databases of normal human tissue, thereby selecting for junctions enriched or even specific to SF3B1-mutant cells. Of these, junctions predicted to create in-frame, rather than out-of-frame, insertions or deletions in their transcripts were selected, thus excluding transcripts expected to be degraded by nonsense mediated mRNA decay. Genes containing the cryptic junctions meeting these criteria were then filtered for those designated as cell surface proteins in the surfaceome database (Town, J. et al. Proc. Natl. Acad. Sci. U.S.A. 2016, 113, 3603-3608). Finally, hits from this database filter were manually curated using literature searches and the Uniprot database (UniProt: the universal protein knowledgebase. Nucleic Acids Res. 2017, 45, 0158-0169) to select those genes where the cryptic insertion or deletion occurs in the extracellular domains of the respective proteins.

Cloning and Expression of MASA cDNAs. Cryptic and canonical isoforms of CD98 and AAVR were amplified from cDNA synthesized from SF3B1-mutant MCF-10A knockin cells, and cloned into overexpression vector pcDNA-DEST47 PINK1 C-GFP (Addgene #13316) by replacing the PINK1 open reading frame with the stop codon-including PCR amplicons in between restriction sites Kpn1 and Not1. Plasmids were transfected into 293T cells with Fugene 6 (Promega), and 48 hours later cells were detached with PBS/EDTA, washed with PBS, stained with goat polyclonal anti-CD98 (sc-7095, Santa Cruz) or mouse polyclonal anti-AAVR (H00079932-B01, Nevus Biologicals) antibodies on ice for 1 hour, washed with PBS, stained with FITC-conjugated anti-goat or anti-mouse secondary antibodies for 30 minutes on ice, washed, and surface fluorescence was obtained with flow cytometry using a FACSCALIBUR and was quantified with FLOWJO.

Example 2

Evidence for a Novel Class of Tumor Surface Antigens Produced by Mutant SF3B1

Figure 5A:
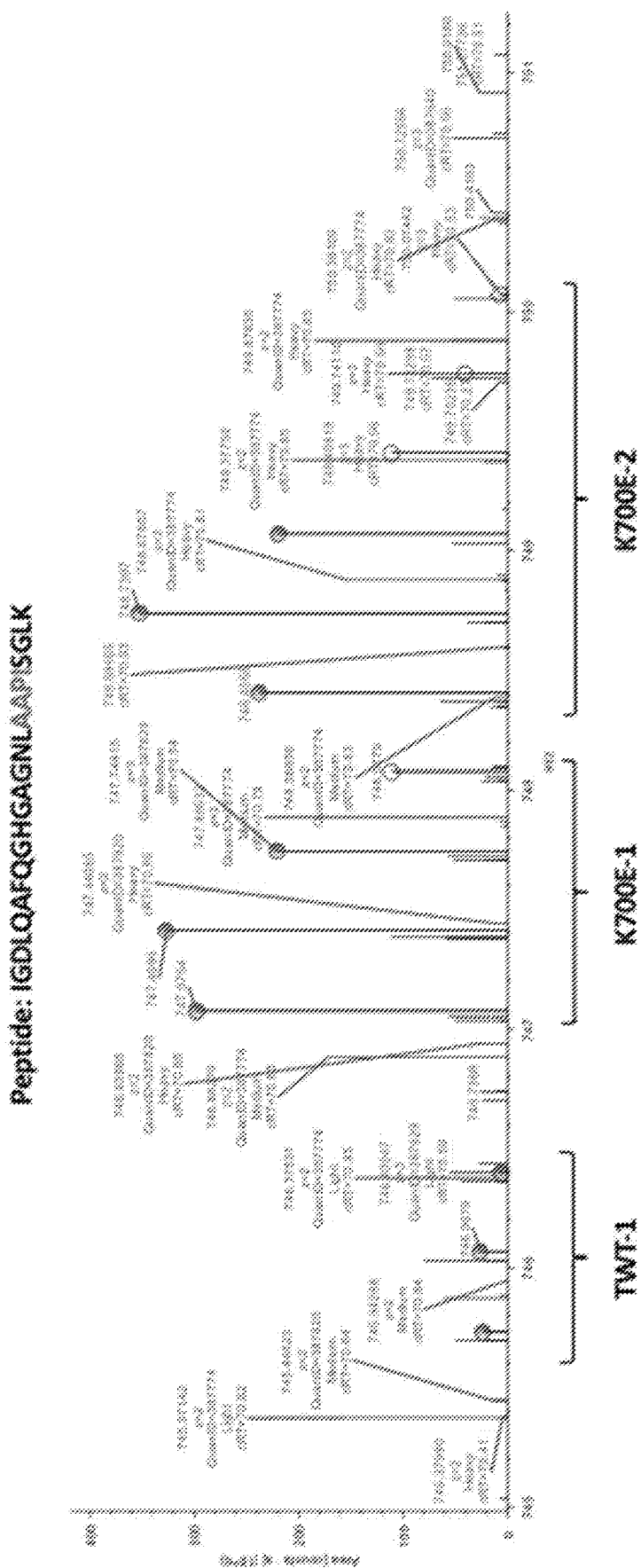
FIG. 5A and FIG. 5B. Evidence for a novel class of tumor surface antigen induced by mutant SF3B1.
Figure 5B:
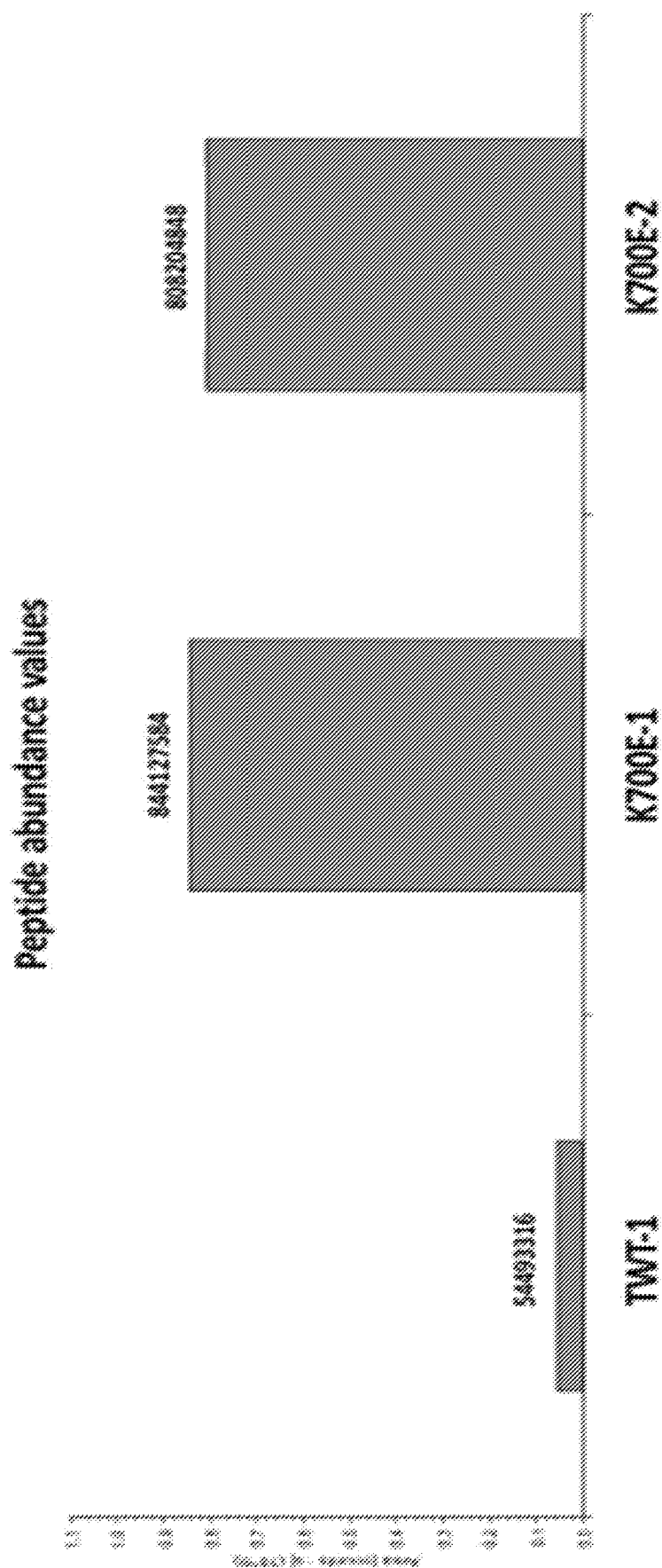
Figure 6:
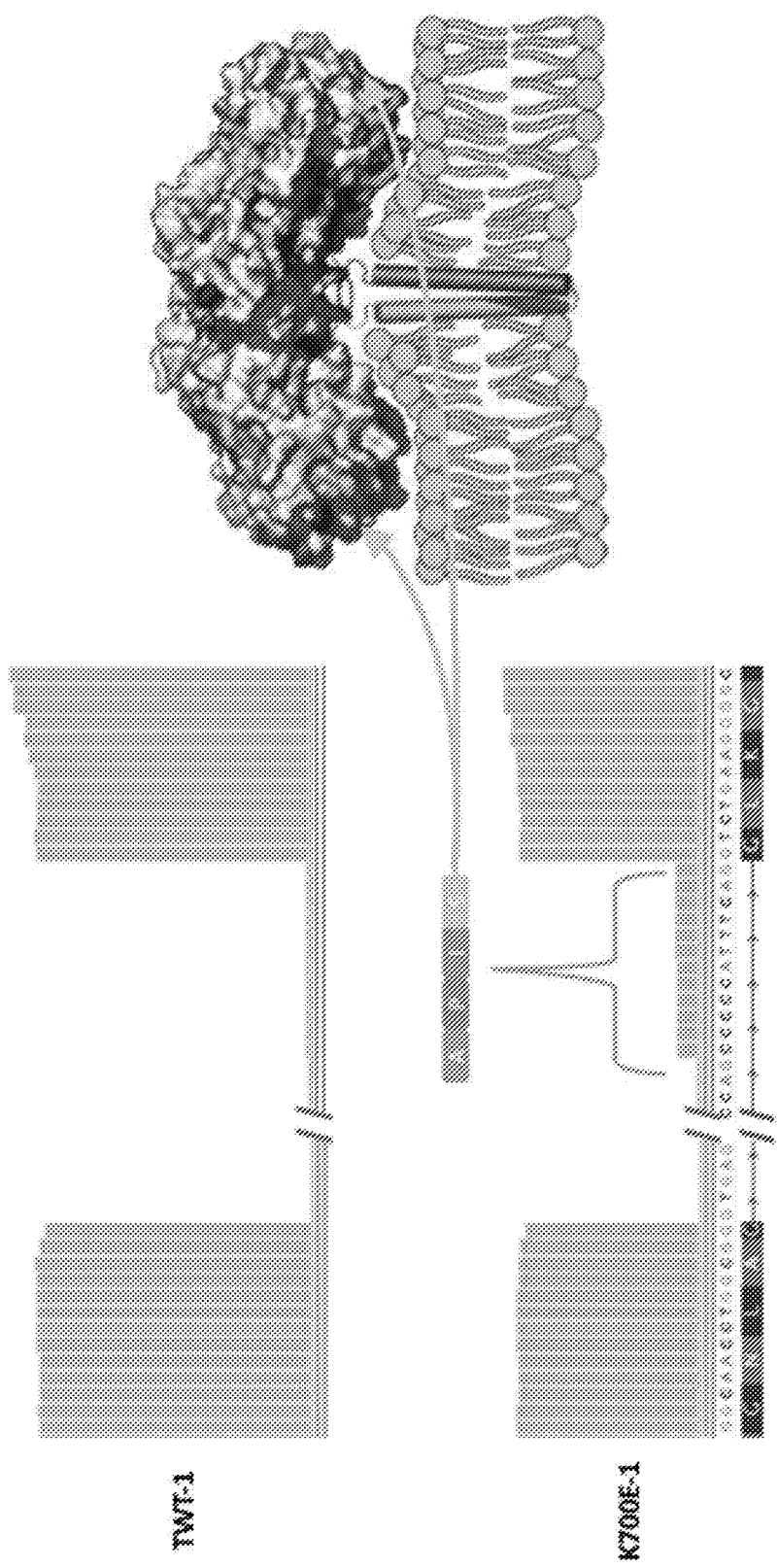
FIG. 6. Cryptic CD98 mRNA is enriched in SF3B1-mutant MCF-10A cells and encodes for an extracellular insertion of 4 amino acids. Left panel: RNA-seq read density plot of exon 4-5 splicing in isogenic MCF-10A cells. Right panel: location of insertion in the dimerized extracellular CD98 protein.

Mass spectrometry data was searched for novel proteins that might arise from cryptic splicing. This search yielded a cryptic isoform of the heavy chain of CD98, also known as SLC3A2. In each SF3B1-mutant clone, abundance values of this cryptic peptide were 16-fold higher than the low-level expression in control cells (FIG. 5B). The cryptic change is an insertion of four amino acids (A-P-1-S), and RNA-seq data showed the corresponding cryptic transcript resulting from alternate 3' splice site selection and insertion of the 12-bp intronic sequence preceding exon 5 that encodes these residues (FIG. 6). Mirroring the peptide-level quantification, the "percent spliced in" (PSI) of this cryptic splice junction was 34-fold higher (11 vs 0.3%, p-value=5.89×10-9) in mutant versus wild-type knockins. Thus, cryptic protein induced by mRNA mis-splicing can indeed be produced and detected in breast epithelial cells following physiologic, heterozygous expression of mutant SF3B1.

Figure 10:
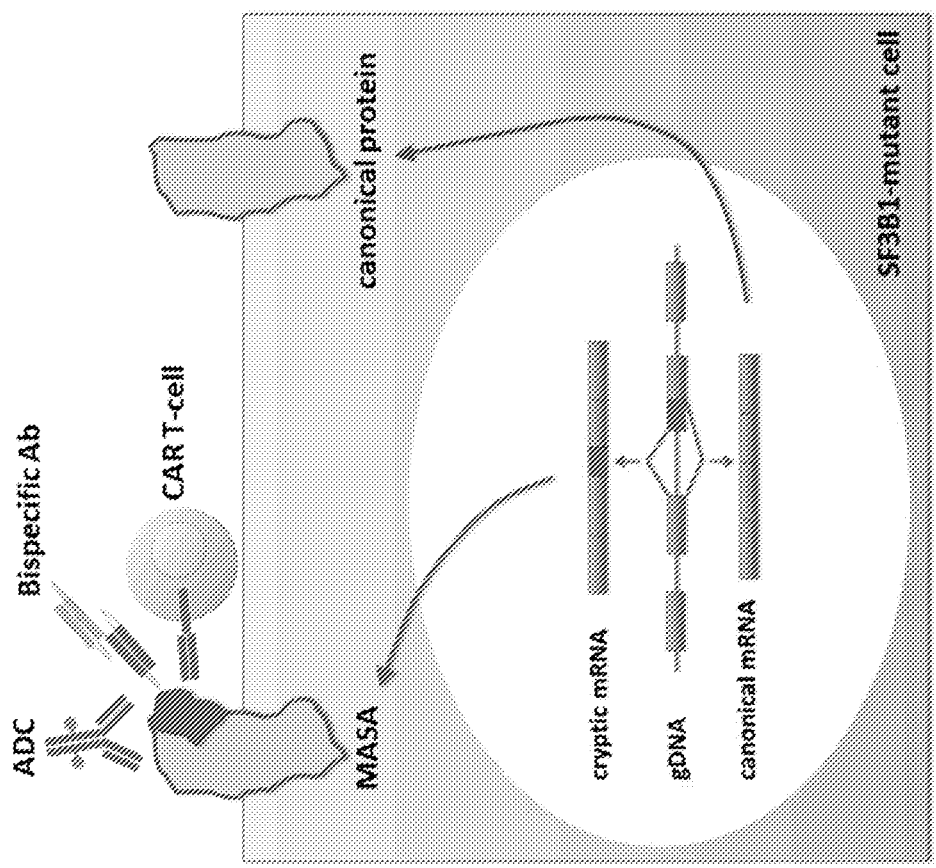
FIG. 10. MASAs represent novel potential targets for antibody- or T-cell-based immunotherapies.

Interestingly, the heavy chain of CD98 is a type II, single-pass transmembrane protein involved in adhesive signaling and amino acid transport (Bajaj, J. et al. Cancer Cell 2016, 30, 792-805), and the observed cryptic insertion resides in the extracellular domain of the protein (FIG. 6). It was concluded that this represents a novel kind of tumor surface antigen namely, a cancer cell-enriched plasma membrane protein with a substantially altered amino acid sequence in its extracellular domain that is produced through cryptic splicing driven by a somatic cancer mutation. By extension, these novel antigens could provide new targets for powerful antibody- and T-cell-based cancer immunotherapies (FIG. 10). Therefore, evidence for additional antigens of this kind was sought. In silico analysis of the RNA-seq data was first performed, as well as analyses of recently published SF3B1-mutant tumors, to identify mis-splicing events predicted to produce in-frame amino acid changes in extracellular domains of proteins that have been identified as part of the "cell surfaceome," utilizing the surfaceome database (Town, J. et al. Proc. Natl. Acad. Sci. U.S.A. 2016, 113, 3603-3608). This analysis identified at least 12 genes predicted to meet these criteria, with cryptic insertions and deletions ranging from 4 to 21 amino acids in length (FIG. 7). These putative proteins were termed MASAs, for Mis-splicing-Associated Surface Antigens.

Figure 8:
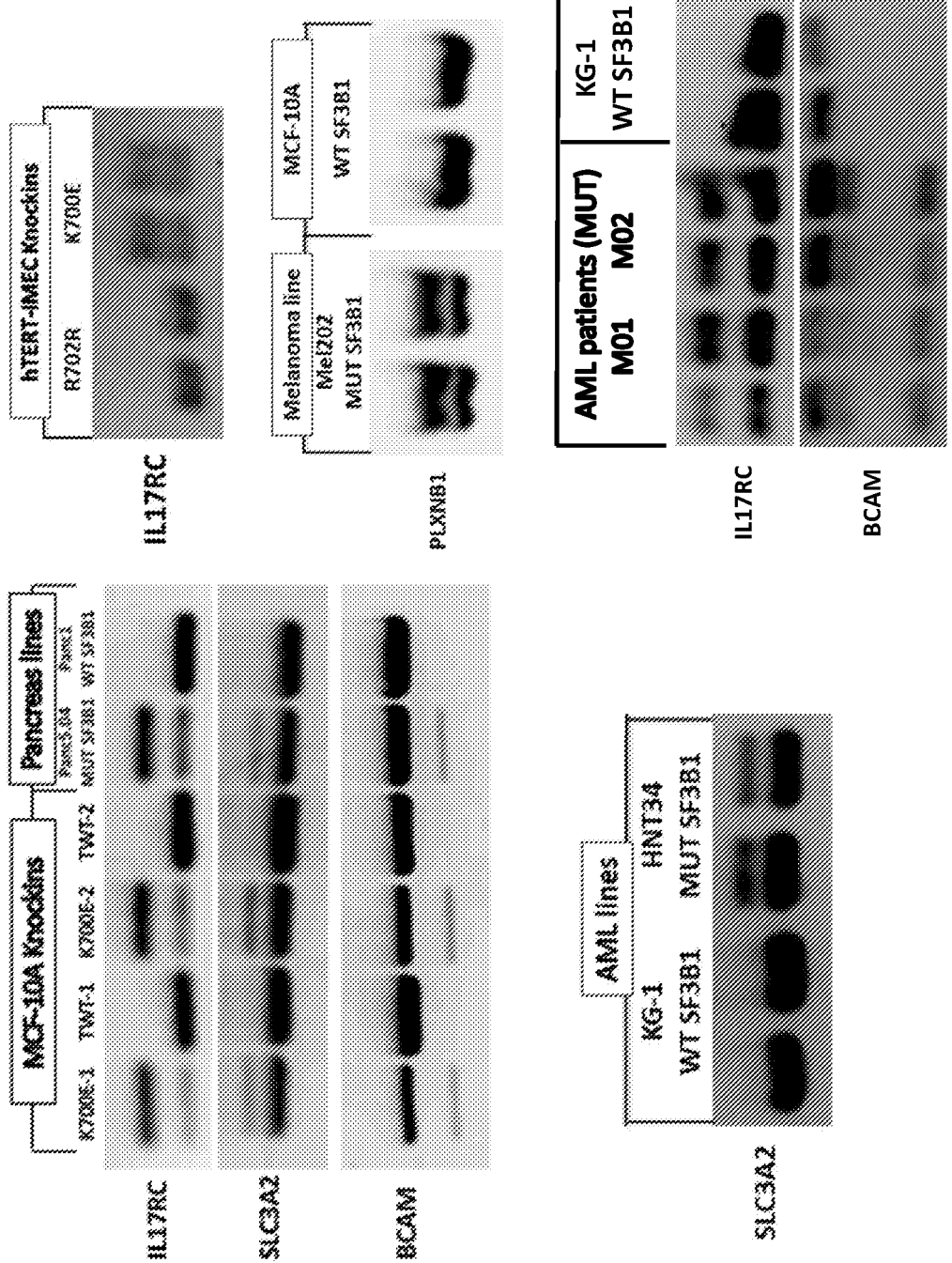
FIG. 8. PCR validation of candidate MASA-encoding splice junctions in diverse SF3B1-mutant cells.
Figure 9:
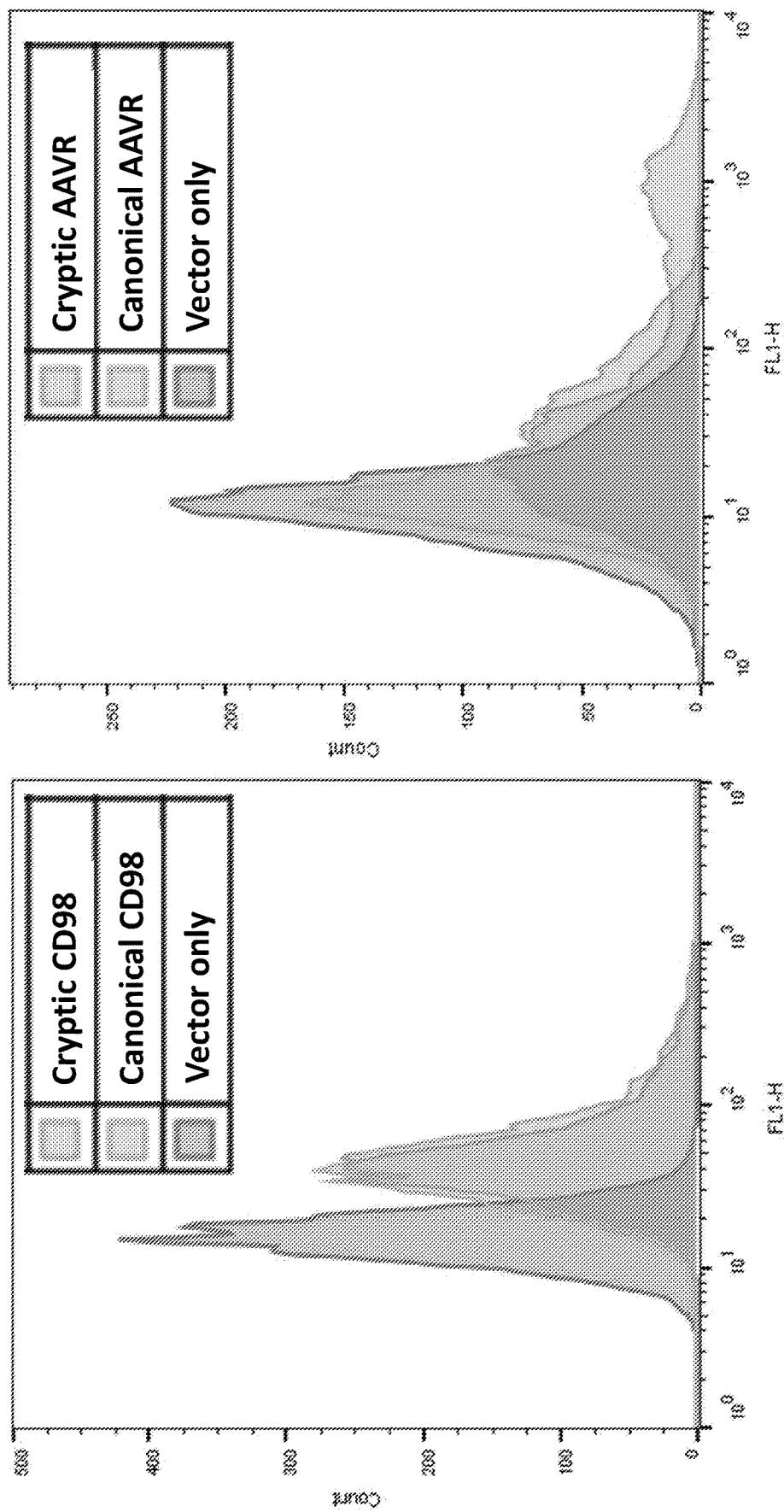
FIG. 9. Cryptic CD98 and AAVR can traffic to the cell membrane and be detected by extracellular antibodies. Histograms of surface fluorescence in 293T cells transfected with MASA-encoding or vector plasmids.

To investigate the extent to which these predicted MASAs are expressed, PCR validation assays were performed on mRNA for the respective cryptic junctions in various SF3B1-mutant samples (FIG. 8). MASA-encoding cryptic splice junctions were present in SF3B1-mutant cell lines from diverse tissues of origin, including pancreatic adenocarcinoma, acute leukemia, uveal melanoma, and the isogenic breast models. Moreover, evidence of MASA-encoding mRNA in peripheral blasts of 2 patients with SF3B1-mutant AML was found. Thus, at the RNA level, MASAs are widely expressed in cancer cells from SF3B1-mutant tumors of diverse lineages.

Finally, to determine whether putative MASAs can be successfully folded and localized to the plasma membrane, functional studies were performed on two candidate MASAs. Canonical and cryptic cDNAs for CD98 and AAVR were cloned, the latter recently shown to be the receptor for adena-associated virus (also known as KIAA0319L). These were then expressed in 293T cells, stained live cells with antibodies not expected to bind the region of cryptic insertion, and detected expression with flow cytometry. As shown in FIG. 5A and FIG. 5B, canonical and cryptic CD98 were detected equally well on the cell surface, in contrast to vector-transfected cells. For AAVR, both proteins on the cell surface were likewise detected, although the signal for cryptic protein was somewhat weaker than canonical. Thus, at least in this overexpression system, MASAs can be successfully trafficked to the cell surface and bound by antibodies in the extracellular space. Taken together, these data provide evidence for the existence and expression of MASAs, and they warrant further studies into these novel and potentially druggable tumor surface antigens.

Evidence for a novel kind of tumor surface antigen was also found, which were named MASAs. Tumor antigens are any molecules sufficiently enriched in cancer cells that they can be distinguished from normal cells by instruments of the immune system (e.g., antibodies and T-cells). Excluding for the moment MHC-restricted peptides (see discussion below), tumor antigens on the cell surface have traditionally included proteins overexpressed through gene amplification (e.g., Her2), proteins overexpressed through less defined mechanisms (e.g., CEA, mesothelin), differentiation antigens restricted to a cell lineage that includes the cancer but whose elimination can be tolerated by the human body (e.g., CD19, CD20), and the few instances of plasma membrane proteins that are recurrently mutated in their extracellular domains (e.g., EGFR viii). These data suggest MASAs could become a novel addition to this list, representing predictable cancer-enriched surface antigens downstream of mis-splicing induced by spliceosome mutations. Admittedly, further work is needed to determine how widely MASAs are translated, folded, and trafficked to the plasma membrane, as well as their abundances in and specificities for-different cancers. Nonetheless, evidence of MASA-encoding mRNAs was found in multiple SF3B1-mutant contexts, as well as MASA protein induced directly by physiologic expression of mutant SF3B1.

It is possible that cryptic CD98 was the one novel protein identified by SILAC largely due to the high overall expression of this gene, as coverage of the proteome by SILAC is inevitably partial and constrained by protein abundance. Likewise, high and ubiquitous tissue expression of CD98 is likely also a major reason why it was the one MASA-encoding mRNA seen in all previous transcriptome analyses of different SF3B1-mutant human tumors (FIG. 7). Along these lines, it was found that MASA-encoding transcripts were broadly detectable across multiple SF3B1-mutant cell lineages with sensitive PCR-based assays, including in some cell types where these transcripts did not reach significance in RNAseq analyses of the same histology, including in the isogenic breast epithelial model (FIG. 7 and FIG. 8). To us, this suggests that if a susceptible pre-mRNA transcript is there to be mis-spliced, mutant SF3B1 will mis-splice it, and tumor-specific differences in detection of these transcripts are more likely influenced by differences in initial gene transcription or technical parameters such as tumor purity, sample size, and sequencing depth than they are by any context-dependent actions of mutant SF3B1 itself. Indeed, it is remarkable just how consistent and specific the mutant SF3B1-induced mis-splicing events are across different cellular contexts, and seemingly across different SF3B1 mutation hotspots. Accordingly, it is possible that, with more sensitive detection methods, such as focused SILAC studies or the development of isoform-specific antibodies, additional MASAs will be identifiable. Furthermore, while this study focused on SF3B1 mutations, MASAs could result from cryptic splicing induced by cancer-associated mutations in other spliceosome proteins, such as U2AF1, and this represents an interesting area for future work.

As tumor surface antigens, MASAs also represent a novel kind of potential drug target. The success of therapeutic monoclonal antibodies, antibody drug conjugates, bispecific antibodies, and CART-cells has been revolutionary in oncology, but there is a great need for more and better tumor surface antigens to target with these technologies. MASAs could offer such targets for spliceosome-mutant cancers, and they would come with certain advantages. First, the predicted MASAs identified varied from their canonical isoforms by 4 to 21 amino acids, significant sequence changes that should facilitate the development of MASA-specific antibodies and chimeric antigen receptors. Second, as MASAs are cancer-enriched versions of natural plasma membrane proteins, they would not require MHC binding nor be restricted to targeting by T-cell mediated immunotherapy in individuals with specific MHC haplotypes. Third, there would theoretically be many MASAs in every spliceosome-mutant cell, providing potential opportunities for sequential or combination targeting, which could address certain mechanisms of possible drug resistance. At the same time, potential pitfalls of targeting MASAs could include inadequate tumor abundance and/or specificity of the antigens, and further work is needed to explore these possibilities. However, advances in the understanding and engineering of antibody drug conjugates, bispecific antibodies, and chimeric antigen receptors suggest that it may be increasingly possible to select and modify the affinities of appropriate targeting modalities to match the tumor abundance and specificity features of the targets. Thus, different MASAs may require different targeting modalities, depending on their abundance and specificity indices. In conclusion, this work suggests MASAs represent an intriguing new kind of potential drug target for spliceosome mutant cancers, and it is possible additional studies are warranted to investigate this therapeutic possibility.

Example 3

Attacking MASAs with Antibody Drug Conjugates

Immunotherapeutic reagents such as monoclonal antibodies, antibody drug conjugates, bispecific antibodies, and chimeric antigen receptor (CAR) T-cells represent some of the most promising therapeutic modalities in oncology. However, all of these therapies need cell surface antigens for their targets. MASAs represent such targets for mSF3B1 cells, and have the advantage of being cancer specific. MASAs are present at the RNA level and, being in-frame, are predicted to make protein, but data on actual protein expression and therefore candidates as antibody targets remain sparse. To answer these questions, isogenic cell lines will be used as previously described (Wu, X. et al. Nat Commun. 2014, 5, 4961; Zahari, M. S. et al. J. Proteome Res. 2015, 14, 3882-3891). To characterize the mSF3B1 proteome, stable isotope labeling by amino acids in cell culture (SILAC)-based liquid chromatography tandem mass spectrometry was performed on the mSF3B1 isogenic cells. This technique provides quantification of differentially expressed peptides in mutant and wild type cells. Then, using the splicing junction analysis of whole transcriptome RNA-seq discussed in Example 3 as a roadmap, the expression of MASAs can be quantified. This will, in turn, allow for prioritizing MASA candidates based on their absolute protein expression level and degree of specificity for SF3B1-mutant cells. This approach may also identify additional MASAs not present in the analysis of publically available RNA-seq data. Candidate MASAs have been identified using this approach including some of the genes shown in FIG. 7 (data not shown). The two validated MASAs with the greatest specificity for SF3B1-mutant cells, the highest absolute protein expression, and proper membrane localization will be selected as candidates for development of MASA-specific antibodies. Monoclonal antibodies against candidate MASAs will be generated (Mohseni, M. et al. Proc. Natl. Acad. Sci. U.S.A. 2014, 111, 17606-17611). Proof of principle studies will be performed to test whether antibody drug conjugates can selectively kill SF3B1-mutant cells (Town, J. et al. Proc. Natl. Acad. Sci. U.S.A. 2016, 113, 3603-3608).

Figure 4:
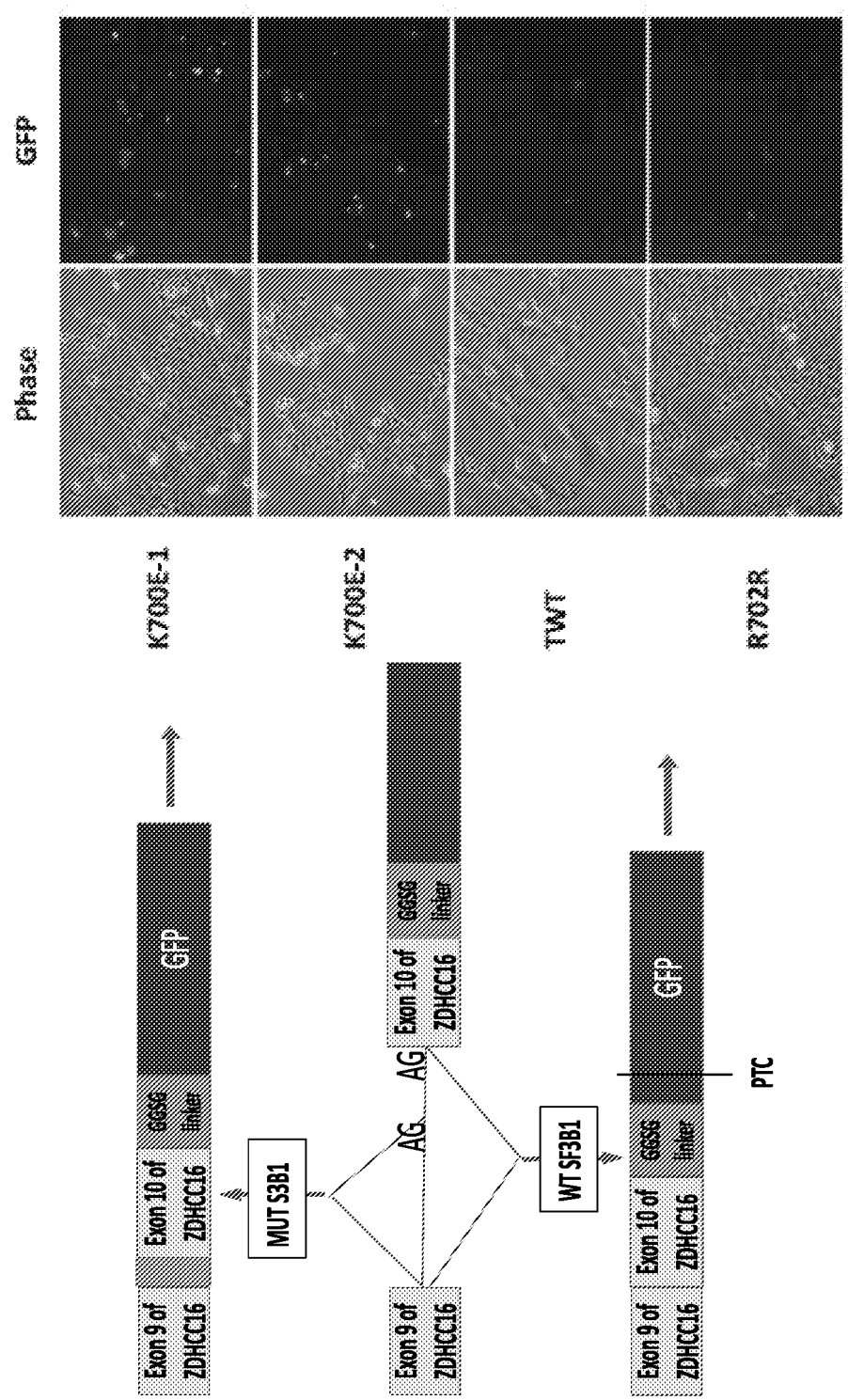
FIG. 4. Strategy of mutant SF3B1 gene expression. Left panel shows constructs made with GFP such that only mutant SF3B1 cells can have an in-frame GFP mRNA and protein expression. Right panel shows GFP expression in mutant SF3B1 cells (K700E-1, -2) but little to no expression in targeted wild-type (TWT) and SNP (R702R) gene targeted control cells.

A "mini-intron" vector was designed utilizing one of the known MASA's intronic sequences as a GFP reporter (FIG. 4). As shown in this experiment, GFP in the mis-spliced open reading frame was detected only in cells with mSF3B1 and not in isogenic wildtype controls. The GFP coding sequence will simply be replaced with that of HER2 (ERBB2) and separately CD19. When stably transduced in mSF3B1 cells, overexpression of these genes will be observed, which will be confirmed by western blot and FACS analysis. In parallel, transfected wildtype and parental controls will only express a small amount of native protein expressed in these cell lines (MCF-10A and hTERT IMECs) since the exogenous HER2 and CD19 transgenes will only be in frame using the cryptic splice acceptor sequence which will not be made in wild type SF3B1 cells. TDM-1 (Kadcyla) and blinatumomab will be obtained, approved antibody drug therapies. TDM-1 will be effective in in vitro cell proliferation cytotoxicity assays only in mSF3B1 tumors by virtue of the fact that they will express HER2 protein whereas wild type control cells will not and therefore be resistant to TDM-1. Similarly, in T-cell cytotoxicity assays, blinatumomab should redirect mSF3B1 cells, but not wild type controls, to T-cells. These experiments will provide a proof of principle prior to the obtainment of MASA specific antibodies. MASA targeting with antibody-drug conjugates would represent a novel therapeutic approach against SF3B1-mutant tumors. Immunoprecipitation followed by peptide identification with mass spec can be performed.

Example 4

Figure 11A:
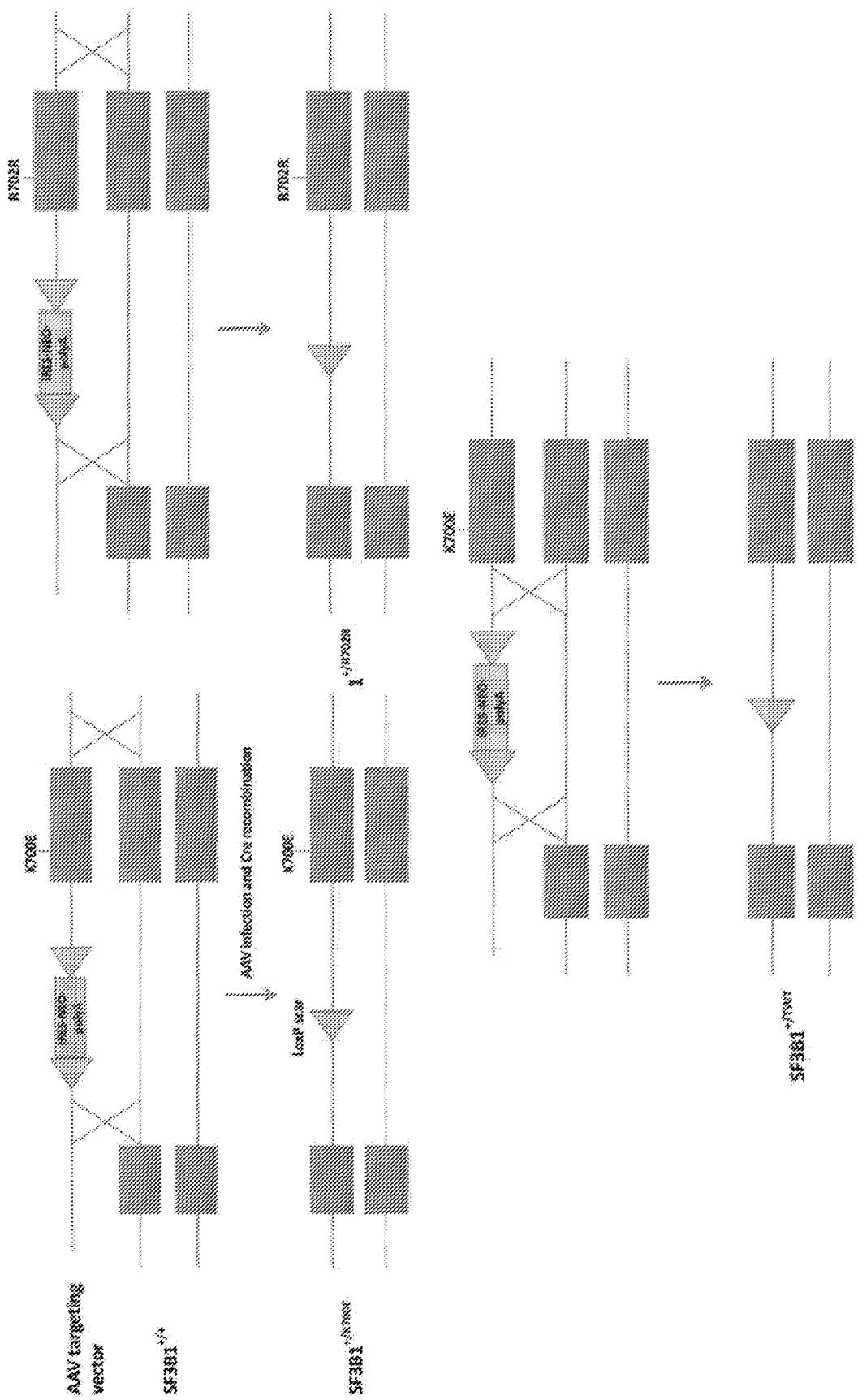
FIG. 11A and FIG. 11B. Creation of isogenic hTERT-IMEC SF3B1K700E breast epithelial cells.
Figure 11B:
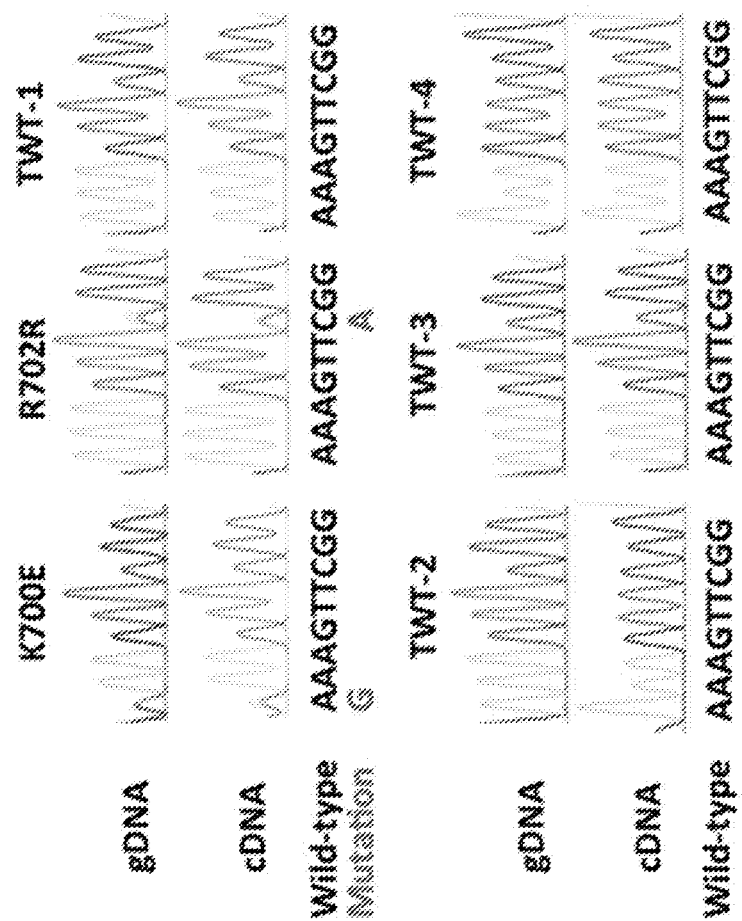

Generation of Cell Models for Detecting MASAs and for Testing MASA-Targeting Therapeutics FIG. 11A and FIG. 11B include representative results of the generation of isogenic hTERT-IMEC SF3B1K700E breast epithelial cells. Mutant or control adeno-associated viruses were used to create heterozygous knockins of K700E, R702R, or targeted wild type (TWT) in hTER-IMEC cells (FIG. 11A). One K700E and five control hTERT-IMEC clones were genotyped by Sanger sequencing (FIG. 11B).

Figure 12B:
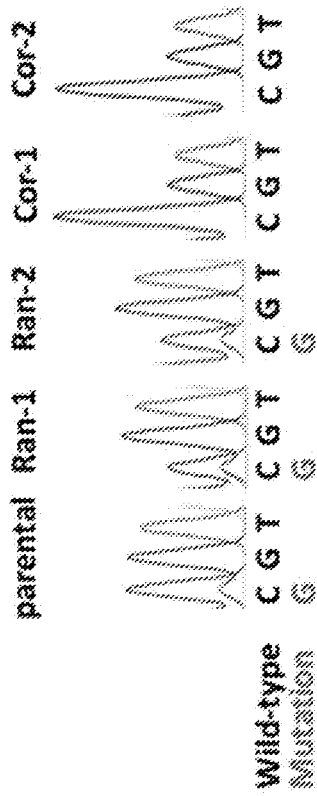
FIG. 12A and FIG. 12B. Creation of clones with inactivation of SF3B1 R625G in Mel202 uveal melanoma cells.
Figure 12A:
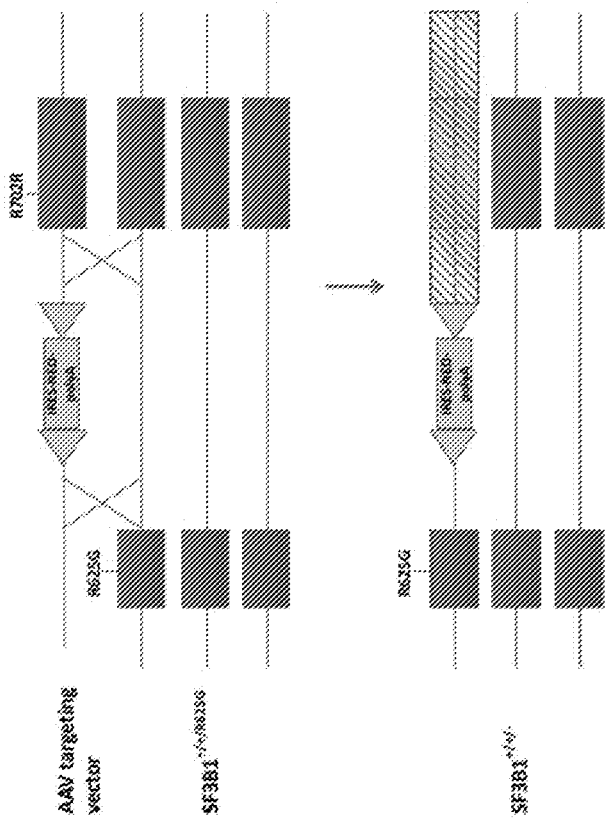
Figure 13:
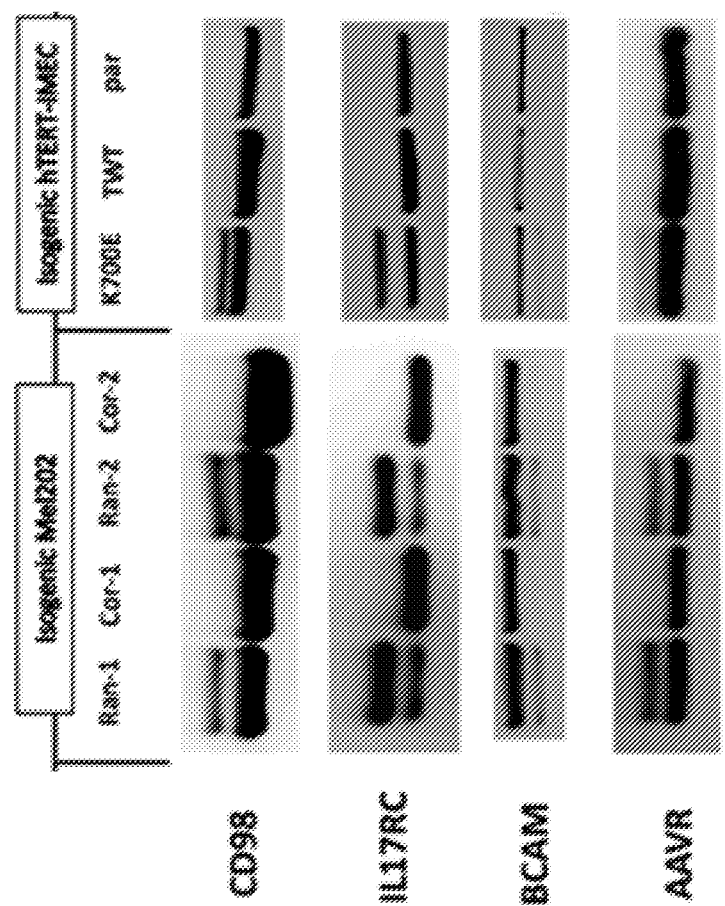
FIG. 13. Detection of MASA mRNAs in hTERT-IMEC and Mel202 isogenic models. PCR-based validation of cryptic CD98, IL17RC, BCAM, and AAVR in isogenic cells. Ran=random integrant, Cor=corrected, TWT=targeted wild type, par=parental.

In addition to the MCF-10A breast epithelial cell knockin models already described, additional isogenic cell models were created for SF3B1 mutations in order to detect MASA mRNAs and create reagents that can be used to test potential MASA-targeting therapies. First, AAV-mediated gene targeting was used to generate an SF3B1K700E knockin clone from human mammary epithelial cells immortalized by telomerase (hTERT-IMECs) (FIG. 11A). To control for nonspecific effects of gene targeting, knockins of a synonymous base substitution at R702 that is a single nucleotide polymorphism (SNP) in the human population were also generated, and "targeted wild type" clones, where cells experience gene targeting but remain wild type (FIG. 11A). Then, to create fully transformed cancer cell models that may be used in vivo as well as in vitro, AAV-mediated gene targeting was used to specifically inactivate the mutant SF3B1 allele in Mel202 uveal melanoma cells, which contain one mutant (R625G) and two wild type alleles of SF3B1 (FIG. 12A). Two of these "corrected" clones were independently isolated, confirming that the R625G mutation was no longer detectable at the mRNA level (FIG. 12B). For controls, clones were utilized in which the targeting cassette integrated randomly in the genome and thus remained mutant for SF3B1. For each of these models, it was found that MASA mRNAs exhibited specificity for the SF3B1-mutant cells (FIG. 13). Thus, these isogenic cell models provide further evidence for the wide tissue distribution of MASAs in spliceosome-mutant cells, and they are novel reagents that will be useful in testing the specificity and therapeutic efficacy of MASA-targeting therapies.

Example 5

Figure 14:
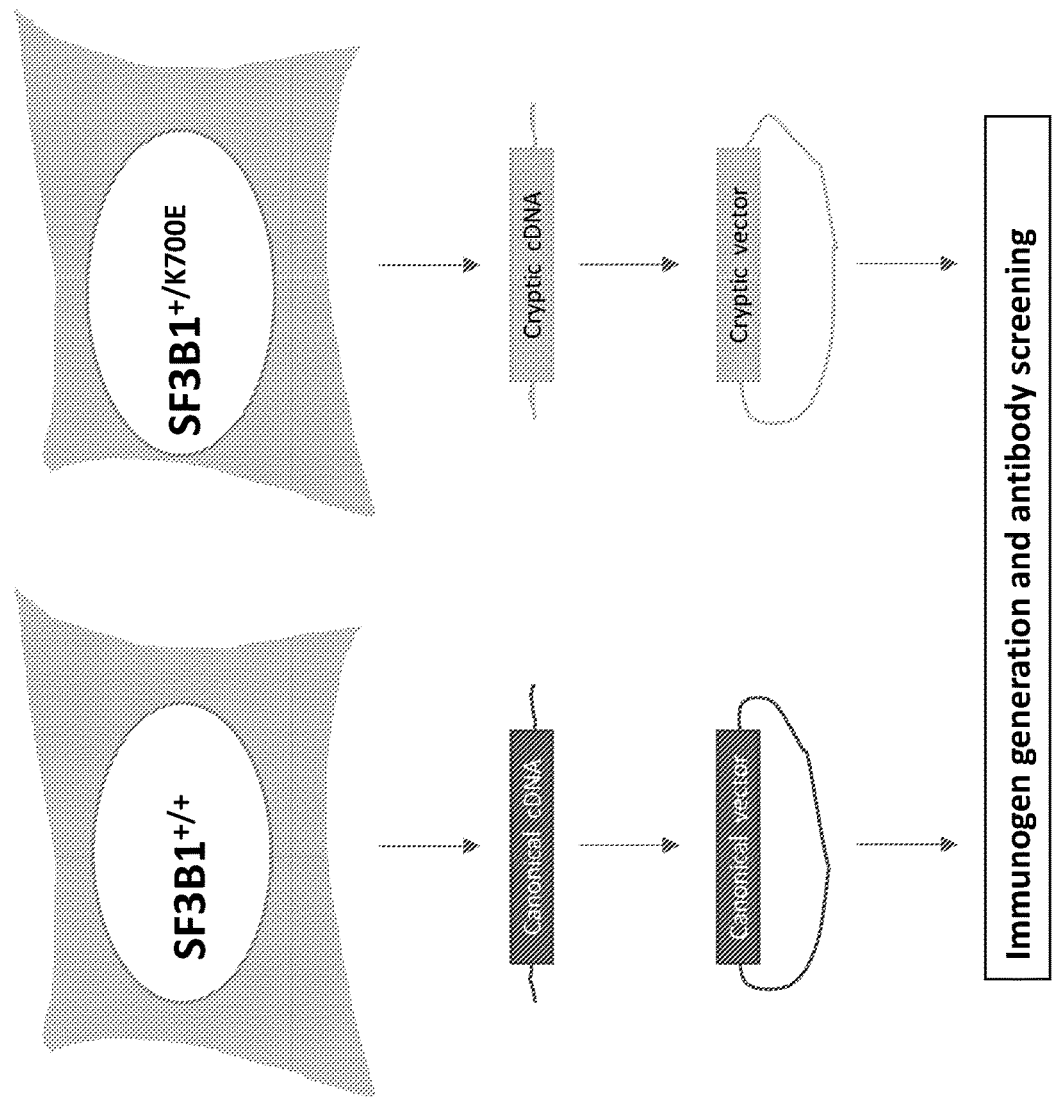
FIG. 14. Generation of MASA cDNA expression constructs for immunogen generation and antibody screening. Cells isogenic for SF3B1 mutation were used for RNA isolation, cDNA synthesis, amplification of canonical and cryptic isoforms of genes for potential MASAs, and cloning of amplicons into cDNA expression vectors for use in immunogen generation and screening of MASA-targeting antibodies.

Generation of MASA-Encoding cDNA Expression Constructs for Use in Generating MASA-Specific Antibodies As part of the process necessary to generate antibodies, which would be one therapeutic modality for targeting MASAs, immunogens representing the cryptic cell surface proteins to be targeted must be themselves created for immunization of animals and eventual screening of antibody candidates. To this end, cDNA expression constructs were engineered of the candidate MASAs for CD98 and AAVR, also known as SLC3A2 and KIAA0319L, respectively. This was done by isolating RNA from our isogenic MCF-10A cells, creating cDNA from it, and amplifying the canonical and cryptic sequences for these two genes (FIG. 14). The amplified sequences were then cloned into expression vectors, and sequences were verified to be correct for the canonical and cryptic isoforms by Sanger sequencing (FIG. 14). These constructs were utilized in the flow cytometry experiments described previously, which demonstrated the cell surface localization of the MASAs CD98 and AAVR. However, these constructs also serve the additional purpose of providing the reagents with which to produce immunogens for generating MASA-targeting antibodies.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A method of identifying a mis-splicing-associated surface antigen (MASA), the method comprising engineering an isogenic cell line to express a spliceosome protein comprising at least one mutation; and identifying at least one mRNA comprising a cryptic splice site in the isogenic cell line; wherein the least one mRNA comprising the cryptic splice site is enriched in the isogenic cell line compared to a parental cell line.

Clause 2. The method of clause 1, wherein the method further comprises identifying at least one MASA polypeptide from a protein encoded by the at least one mRNA comprising the cryptic splice site, wherein the protein is generated by virtue of activity of the mutated spliceosome protein.

Clause 3. The method of clause 1 or clause 2, wherein spliceosome protein is selected from SF3B1, U2AF1, SRSF2, ZRSR2, RBM10, FUBP1, and any derivatives or variations thereof.

Clause 4. The method of clause 1 or clause 2, wherein the spliceosome protein is SF3B1 and any derivatives or variations thereof.

Clause 5. The method of clause 4, wherein the spliceosome protein is SF3B1, and wherein the at least one mutation alters an amino acid at position E622, Y623, R625, N626, W658, H662, T663, K666, Q698, Q699, K700, V701, R702, I704, S705, A706, G740, K741, G742, R775, E776, D781, M784, K785, I787, D894, E902, or a combination thereof.

Clause 6. The method of clause 4, wherein the spliceosome protein is SF3B1, and wherein the at least one mutation produces one of the following amino acid substitutions: E622Q, N626D, K666E, K666Q, K700E, and D781E, or a combination thereof.

Clause 7. The method of clause 4, wherein the spliceosome protein is SF3B1, and wherein the at least one mutation produces amino acid substitution K700E.

Clause 8. The method of any of clause 1 to 7, wherein the mutation comprises an in-frame insertion.

Clause 9. The method of any of clause 1 to 7, wherein the mutation comprises an in-frame deletion.

Clause 10. The method of any of clause 1 to 9, wherein the at least one mRNA comprising the cryptic splice site is selected from CD98 (SLC3A2), BCAM, BSG, IL17RC, IL6ST, ITFG3, KIAA0319L, LY75, NOM01, PLXNB1, TFRC, IGFR1, and IL6ST.

Clause 11. The method of clause 10, wherein the method further comprises identifying at least one MASA on a protein encoded by the at least one mRNA selected from CD98 (SLC3A2), BCAM, BSG, IL17RC, IL6ST, ITFG3, KIAA0319L, LY75, NOM01, PLXNB1, TFRC, IGFR1, and IL6ST.

Clause 12. The method of any of clauses 1 to 11, wherein the isogenic cell line is selected from a mammalian cell line, a non-mammalian cell line, a human cell line, a primary human cell line, a transformed cell line, a transformed human cell line, cancerous cell line, a primary tumor cell line, and a breast cancer epithelial cell line.

Clause 13. The method of any of clauses 1 to 11, wherein the isogenic cell line is selected from MCF-10A cells, hTERT cells, hTERT-IMEC cells, and Mel202 uveal melanoma cells.

Clause 14. A construct for expressing the spliceosome protein of any of clauses 1 to 13.

Clause 15. A construct for expressing the at least one mRNA comprising the cryptic splice site of clause 1 or clause 2.

Clause 16. A construct for expressing the at least one MASA polypeptide of clause 2.

Clause 17. An isogenic cell line engineered to express a spliceosome protein comprising at least one mutation, wherein the isogenic cell line is enriched for at least one mRNA comprising a cryptic splice site as compared to a parental cell line due to expression of the mutated spliceosome protein.

Clause 18. The isogenic cell line of clause 17, wherein the at least one mRNA comprising the cryptic splice site encodes for a protein comprising a mis-splicing-associated surface antigen (MASA) polypeptide.

Clause 19. The isogenic cell line of clause 17 or clause 18, wherein the spliceosome protein is selected from SF3B1, U2AF1, SRSF2, ZRSR2, SF3A1, U2AF2, and any derivatives or variations thereof.

Clause 20. The isogenic cell line of clause 17 or clause 18, wherein the spliceosome protein is SF3B1, and wherein the at least one mutation alters an amino acid at position E622, Y623, R625, N626, W658, H662, T663, K666, Q698, Q699, K700, V701, R702, 1704, S705, A706, G740, K741, G742, R775, E776, D781, M784, K785, 1787, D894, E902, or a combination thereof.

Clause 21. The isogenic cell line of any of clauses 17 to 20, wherein the at least one mRNA comprising the cryptic splice site is selected from CD98 (SLC3A2), BCAM, BSG, IL17RC, IL6ST, ITFG3, KIAA0319L, LY75, NOM01, PLXNB1, TFRC, IGFR1, and IL6ST.

Clause 22. The isogenic cell line of any of clauses 17 to 21, wherein the isogenic cell line is selected from a mammalian cell line, a non-mammalian cell line, a human cell line, a primary human cell line, a transformed cell line, a transformed human cell line, cancerous cell line, a primary tumor cell line, and a breast cancer epithelial cell line.

Clause 23. The isogenic cell line of any of clauses 17 to 21, herein the isogenic cell line is selected from MCF-10A cells, hTERT cells, hTERT-IMEC cells, and Mel202 uveal melanoma cells.

Clause 24. A method for identifying a modulating agent of a mis-splicing-associated surface antigen (MASA), the method comprising engineering an isogenic cell line to express a spliceosome protein comprising at least one mutation, wherein the isogenic cell line is enriched for a protein comprising at least one MASA polypeptide as compared to a parental cell line due to expression of the mutated spliceosome protein; isolating the protein comprising the at least one MASA polypeptide; and screening a plurality of modulating agents for binding to the at least one MASA polypeptide.

Clause 25. The method of clause 24, wherein the plurality of modulating agents comprises one or more of an antibody, a polyclonal antibody, a monoclonal antibody, single-chain variable fragment, a bi-specific antibody, or an antigen binding fragment thereof.

What is claimed is:

1. A method of identifying a mis-splicing associated surface antigen (MASA), the method comprising:
   engineering an isogenic cell line to express a mutant spliceosome protein;
   identifying in the isogenic cell line a protein comprising a MASA polypeptide comprising a tumor surface antigen,
   wherein the MASA polypeptide is encoded by a CD98 or AAVR mRNA comprising a cryptic splice site and mis-splicing of the mRNA produces a mis-spliced mRNA comprising an in-frame insertion or an in-frame deletion in a nucleotide sequence encoding an extracellular domain of the protein; and
   detecting expression of a cryptic CD98 or cryptic AAVR protein comprising the MASA polypeptide on the surface of the isogenic cell line,
   wherein the MASA polypeptide is enriched in the isogenic cell line compared to a parental cell line.

2. The method according to claim 1, wherein the method further comprises isolating the cryptic CD98 or cryptic AAVR protein comprising the MASA polypeptide.

3. The method according to claim 1, wherein the mutant spliceosome protein is selected from SF3B1, U2AF1, SRSF2, ZRSR2, RBM10, FUBP1, and any derivatives or variations thereof.

4. The method according to claim 3, wherein the mutant spliceosome protein is SF3B1 or any derivatives or variations thereof.

5. The method according to claim 4, wherein the mutant spliceosome protein is SF3B1 comprising an alteration in an amino acid at position E622, Y623, R625, N626, W658, H662, T663, K666, Q698, Q699, K700, V701, R702, 1704, S705, A706, G740, K741, G742, R775, E776, D781, M784, K785, 1787, D894, E902, or a combination thereof.

6. The method according to claim 4, wherein the mutant spliceosome protein is SF3B1 comprising one of the following amino acid substitutions: E622Q, N626D, K666E, K666Q, K700E, and D781E, or a combination thereof.

7. The method according to claim 4, wherein the spliceosome protein is SF3B1 comprising amino acid substitution K700E.

8. The method according to claim 1, wherein the mutant spliceosome protein comprises an in-frame insertion or an in-frame deletion.

9. The method according to claim 1, wherein the isogenic cell line is selected from a mammalian cell line, a non-mammalian cell line, a human cell line, a primary human cell line, a transformed cell line, a transformed human cell line, cancerous cell line, a primary tumor cell line, and a breast cancer epithelial cell line.

10. The method according to claim 1, wherein the isogenic cell line is selected from MCF-10A cells, hTERT cells, hTERT-IMEC cells, and Mel202 uveal melanoma cells.

11. A method for identifying a modulating agent of a mis-splicing-associated surface antigen (MASA), the method comprising:
   engineering an isogenic cell line to express a spliceosome protein comprising at least one mutation, wherein the isogenic cell line is enriched for a protein comprising a MASA polypeptide comprising a tumor surface antigen; and wherein the MASA polypeptide is encoded by a CD98 or AAVR mRNA comprising a cryptic splice site and mis-splicing of the mRNA produces a mis-spliced mRNA comprising an in-frame insertion or an in-frame deletion in a nucleotide sequence encoding an extracellular domain of the protein;
   detecting expression of a cryptic CD98 or cryptic AAVR protein comprising the MASA polypeptide on the surface of the isogenic cell line;
   isolating the cryptic CD98 or cryptic AAVR protein comprising the MASA polypeptide; and
   screening a plurality of modulating agents for binding to the MASA polypeptide.

12. The method according to claim 11, wherein the plurality of modulating agents comprises one or more of an antibody, a polyclonal antibody, a monoclonal antibody, single chain variable fragment, a bi-specific antibody, or an antigen binding fragment thereof.

* * * * *

UNITED STATES PATENT AND TRADEMARK OFFICE
CERTIFICATE OF CORRECTION

| | | |
|---|---|---|
| PATENT NO. | : 12,098,172 B2 | Page 1 of 1 |
| APPLICATION NO. | : 16/635861 | |
| DATED | : September 24, 2024 | |
| INVENTOR(S) | : William Brian Dalton, Ben Ho Park and Eric Christenson | |

It is certified that error appears in the above-identified patent and that said Letters Patent is hereby corrected as shown below:

In the Claims

Claim 5, Column 24, Line 53 reads:
"H662, T663, K666, Q698, Q699, K700, V701, R702, 1704,"
Whereas it should read:
"H662, T663, K666, Q698, Q699, K700, V701, R702, I704," and Claim 5, Column 24, Line 55 reads:
"K785, 1787, D894, E902, or a combination thereof."
Whereas it should read:
"K785, I787, D894, E902, or a combination thereof."

Signed and Sealed this
Seventh Day of January, 2025

Derrick Brent
*Acting Director of the United States Patent and Trademark Office*